US012122717B2

(12) United States Patent
Hess et al.

(10) Patent No.: US 12,122,717 B2
(45) Date of Patent: Oct. 22, 2024

(54) COMPOSITIONS AND METHODS FOR ADHESION TO SURFACES

(71) Applicant: RevBio, Inc., Lowell, MA (US)

(72) Inventors: Brian J. Hess, Charlestown, MA (US); George W. Kay, Sharon, MA (US)

(73) Assignee: RevBio, Inc., Lowell, MA (US)

( * ) Notice: Subject to any disclaimer, the term of this patent is extended or adjusted under 35 U.S.C. 154(b) by 0 days.

(21) Appl. No.: 17/561,657

(22) Filed: Dec. 23, 2021

(65) Prior Publication Data

US 2022/0194849 A1 Jun. 23, 2022

Related U.S. Application Data

(63) Continuation of application No. 16/324,319, filed as application No. PCT/US2017/045971 on Aug. 8, 2017, now Pat. No. 11,247,941.

(Continued)

(51) Int. Cl.
| | |
|---|---|
| *C04B 12/02* | (2006.01) |
| *A61K 6/864* | (2020.01) |
| *A61K 6/889* | (2020.01) |
| *A61K 31/197* | (2006.01) |
| *A61K 45/06* | (2006.01) |
| *A61L 24/00* | (2006.01) |
| *A61L 24/02* | (2006.01) |
| *A61L 24/06* | (2006.01) |
| *C04B 24/04* | (2006.01) |
| *C04B 24/12* | (2006.01) |
| *C04B 111/00* | (2006.01) |

(52) U.S. Cl.
CPC ............ *C04B 12/025* (2013.01); *A61K 6/864* (2020.01); *A61K 6/889* (2020.01); *A61K 31/197* (2013.01); *A61K 45/06* (2013.01); *A61L 24/001* (2013.01); *A61L 24/0015* (2013.01); *A61L 24/02* (2013.01); *A61L 24/06* (2013.01); *C04B 24/04* (2013.01); *C04B 24/123* (2013.01); *A61L 2300/102* (2013.01); *A61L 2300/404* (2013.01); *A61L 2300/41* (2013.01); *A61L 2300/442* (2013.01); *A61L 2300/802* (2013.01); *C04B 2111/00836* (2013.01)

(58) Field of Classification Search
CPC ...................................................... A61L 24/02
See application file for complete search history.

(56) References Cited

U.S. PATENT DOCUMENTS

| | | | |
|---|---|---|---|
| 4,758,612 A | 7/1988 | Wilson et al. | |
| 4,902,649 A | 2/1990 | Kimura et al. | |

(Continued)

FOREIGN PATENT DOCUMENTS

| | | |
|---|---|---|
| CN | 102307941 A | 1/2012 |
| EP | 1721949 A1 | 11/2006 |

(Continued)

OTHER PUBLICATIONS

Dinarvand et al. "Polylactide-co-glycolide nanoparticles for controlled delivery of anticancer agents" International Journal of Nanomedicine, 2011, vol. 6, pp. 877-895.

(Continued)

*Primary Examiner* — Michael F Pepitone

(57) ABSTRACT

Provided herein are compositions and their methods of use to adhere (e.g., in wet and dry environments) a variety of materials together.

16 Claims, 9 Drawing Sheets

Related U.S. Application Data

(60) Provisional application No. 62/371,946, filed on Aug. 8, 2016.

(56) References Cited

U.S. PATENT DOCUMENTS

| | | | |
|---|---|---|---|
| 5,180,426 | A | 1/1993 | Sumita |
| 6,087,553 | A | 7/2000 | Cohen et al. |
| 10,286,102 | B2 | 5/2019 | Garigapati et al. |
| 11,247,941 | B2 * | 2/2022 | Hess ............... A61K 31/197 |
| 2002/0123750 | A1 | 9/2002 | Eisermann et al. |
| 2005/0217538 | A1 | 10/2005 | Reinstorf et al. |
| 2007/0221093 | A1 | 9/2007 | Erdrich et al. |
| 2010/0015068 | A1 | 1/2010 | Karp et al. |
| 2011/0152195 | A1 | 6/2011 | O'Mahony et al. |
| 2011/0277931 | A1 | 11/2011 | Garigapati et al. |
| 2011/0287067 | A1 | 11/2011 | Stewart |
| 2012/0082705 | A1 | 4/2012 | Garigapati et al. |
| 2012/0288446 | A1 * | 11/2012 | Garigapati ............ A61L 24/04 424/9.1 |
| 2013/0122057 | A1 | 5/2013 | Garigapati et al. |
| 2013/0238027 | A1 | 9/2013 | Zhang et al. |
| 2013/0264244 | A1 | 10/2013 | O'Mahony et al. |
| 2014/0093549 | A1 | 4/2014 | Van Holten et al. |
| 2015/0072315 | A1 | 3/2015 | Busch et al. |

FOREIGN PATENT DOCUMENTS

| | | |
|---|---|---|
| JP | H01279815 A | 11/1989 |
| WO | 9945890 A1 | 9/1999 |
| WO | 2004/103419 A1 | 12/2004 |
| WO | 2008/075824 A1 | 6/2008 |
| WO | 2011/143226 A1 | 11/2011 |

OTHER PUBLICATIONS

International Search Report and Written Opinion for International Application No. PCT/US2017/013256 dated May 25, 2017.
International Search Report and Written Opinion for International Application No. PCT/US2017/045971 dated Oct. 24, 2017.
John L. Meyer et al: "The Influence of Multidentate Organic Phosphonates on the Crystal Growth of Hydroxyapatite," Calcified Tissue International, vol. 13, (1973), pp. 295-303.
Kazuhi Ko Kandori et al: "Texture and Formation Mechanism of Fibrous Calcium Hydroxyapatite Particles Prepared by Decomposition of Calcium-EDTA Chelates," Journal of the American Ceramic Society, vol. 30, No. 5, (1997), pp. 1157-1164.
Partial European Search Report for European Patent Application No. 17738974.9 dated Aug. 27, 2019.

* cited by examiner

COMPOSITIONS AND METHODS FOR ADHESION TO SURFACES

CROSS REFERENCE TO RELATED APPLICATIONS

This application claims priority under 35 U.S.C. § 120 as a continuation of U.S. patent application Ser. No. 16/324,319, filed Feb. 8, 2019, issued as U.S. Pat. No. 11,247,941, which is a U.S. National Stage Application under 35 U.S.C. § 371 of International Application No. PCT/US2017/045971, filed Aug. 8, 2017, which claims priority under 35 U.S.C. § 119(e) to U.S. Provisional Application Ser. No. 62/371,946, filed on Aug. 8, 2016. The entire contents of each of the foregoing applications are incorporated herein by reference. U.S. patent application Ser. No. 16/324,319, also claims priority to International Application No. PCT/US2017/013256, filed on Jan. 12, 2017, which is herein incorporated by reference in its entirety.

FIELD OF TECHNOLOGY

Aspects and embodiments disclosed herein relate to adhesive compositions and methods of use thereof. More particularly, aspects and embodiments disclosed herein relate to adhesive compositions and their use in medical and industrial applications.

BACKGROUND

Fixation and maintenance of spatial relationships of wet objects, especially in orthopedics (e.g., broken bones, implants to bone, artificial joints to bone, sub-parts of prostheses to one another, such as dental crown to dental implant, etc.) have been a desirable goal. To that end mechanical devices, such as bone screws, nails and bone cements have been developed and used for decades. The limitations of these devices are significant. Hardware devices may require bone pieces to be large enough for drilling and strong and elastic enough to withstand concentrated mechanical stresses and drilling. Resin-based cements are non-biodegradable and potentially toxic, while not adhering to wet surfaces.

Water-based self-setting calcium phosphate cements (CPCs) have been limited by at least three shortcomings: they are not adhesive, they are relatively weak intrinsically, and they are generally formulated as particulates or thick slurries, which may not be injectable.

In general industrial settings, the need to stabilize mechanical relationships between elements (e.g., nuts and bolts, pipes and fittings, compression plates, bulkhead fittings, etc.) of structures subjected to vibration, cyclical straining, or other dislodging conditions has been a challenge. The need has partially been addressed by devices on the market, such as lock washers, a wide range of lock nut designs (e.g., prevailing torque nut, K-nut, castellated nut, serrated flange nut, distorted thread nut, etc.), thread-locking fluid products (e.g., plumber's paste, Loctite® (Düsseldorf, Germany) products), and selection of materials with specific hardness and elasticity characteristics. However, the application of these methods is often limited to certain environments and excluded from other, more challenging, ones such as wet or submerged field (e.g., underwater use on drilling platforms, bridges, pipelines, vessel hulls, etc.).

SUMMARY OF INVENTIONS

Provided herein are adhesive, self-setting compositions, which feature an interaction between a small molecule anionic reactant and a mineral salt of a multivalent metal in an aqueous medium. Further provided herein are adhesive compositions comprising a mixture of a compound of a Formula (e.g., Formula (I), Formula (II), Formula (III), Formula (IV), or combinations thereof), a mineral salt of a multivalent metal, and an aqueous medium.

Exemplary multivalent metal salts may be organic or inorganic in nature and include calcium phosphates (e.g., hydroxyapatite, octacalcium phosphate, tetra-calcium phosphate, tricalcium phosphate), calcium nitrate, calcium citrate, calcium carbonate, magnesium phosphates, sodium silicates, lithium phosphates, titanium phosphates, strontium phosphates, barium phosphates, zinc phosphates, calcium oxide, magnesium oxide, and combinations thereof. Exemplary multivalent metal salts may be a salt of an alkaline earth element (e.g., beryllium, magnesium, barium, radium, strontium, or calcium).

In an aspect, provided herein are adhesive compositions comprising a multivalent metal salt (e.g., tetra-calcium phosphate), a compound of Formula (I), and an aqueous medium, wherein the compound of Formula (I) is:

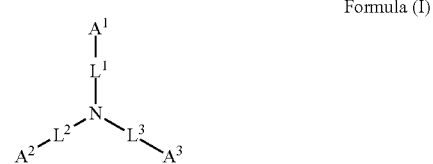

Formula (I)

wherein: each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene).

In some embodiments, each of $A^1$, $A^2$, and $A^3$ is independently a carboxyl or phosphonyl. In some embodiments, $A^1$ is carboxyl, and $A^2$ and $A^3$ are phosphonyl. In some embodiments, $A^1$, $A^2$ and $A^3$ are phosphonyl.

In some embodiments, each of $L^1$, $L^2$, and $L^3$ is $C_1$-$C_3$ alkylene. In some embodiments, each of $L^1$, $L^2$, and $L^3$ is $C_1$ alkylene.

In some embodiments, the compound of Formula (I) is a compound of Formula (I-a) or (I-b):

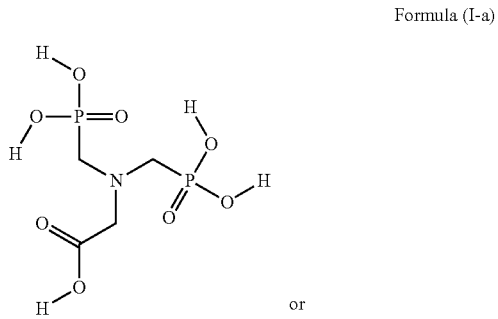

Formula (I-a)

or

-continued

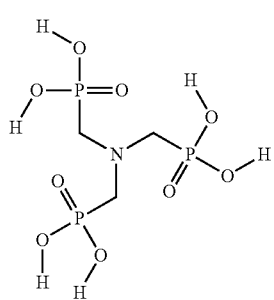
Formula (I-b)

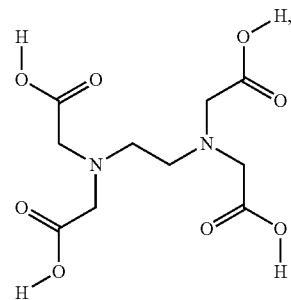
Formula (II-a)

In some embodiments, the aqueous medium is water.

In some embodiments, the composition further comprises an additive.

In another aspect, provided herein are adhesive compositions comprising a multivalent metal salt (e.g., tetracalcium phosphate), a compound of Formula (II), and an aqueous medium, wherein the compound of Formula (II) is:

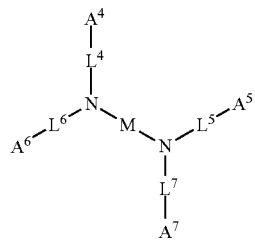
Formula (II)

wherein: each of $A^4$, $A^5$, and $A^6$, is independently selected from an acidic group (e.g., a carboxyl or phosphonyl); $A^7$ is selected from an acidic group (e.g., a carboxyl or phosphonyl), a hydrogen atom, an alkyl, an aryl, a hydroxy group, a thio group, and an amino group; each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In some embodiments, $A^4$, $A^5$, $A^6$ and $A^7$ are carboxyl.

In some embodiments, $L^4$, $L^5$, $L^6$, and $L^7$ are $C_1$-$C_3$ alkylene. In some embodiments, $L^4$, $L^5$, $L^6$, and $L^7$ are $C_1$ alkylene.

In some embodiments, M is $C_1$-$C_4$ alkylene. In some embodiments, M is $C_2$ alkylene. In some embodiments, M is $C_3$ alkylene. In some embodiments, M is $C_1$-$C_6$ heteroalkylene. In some embodiments, M is $C_6$ heteroalkylene. In some embodiments, M is bis(ethyleneoxy)ethylene. In some embodiments, M includes side chains. In some embodiments, M includes multiple side chains. In some embodiments, M includes one or multiple carboxymethylene side chains. In some embodiments, M includes one or multiple N-carboxymethylene groups or N-hydroxymethylene groups.

In some embodiments, the compound of Formula (II) includes three, four, five, six, or more N-carboxymethylene groups.

In some embodiments, the compound of Formula (II) comprises ethylenediamine tetraacetic acid (EDTA).

In some embodiments, the compound of Formula (II) is a compound of Formula (II-a), (II-b), (II-c), (II-d), (II-e), or (II-f):

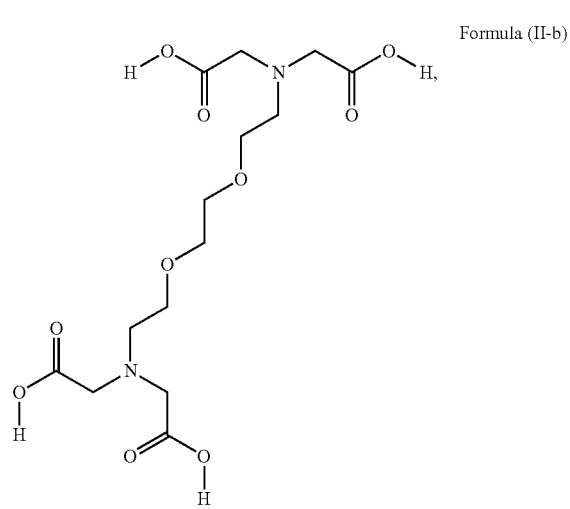
Formula (II-b)

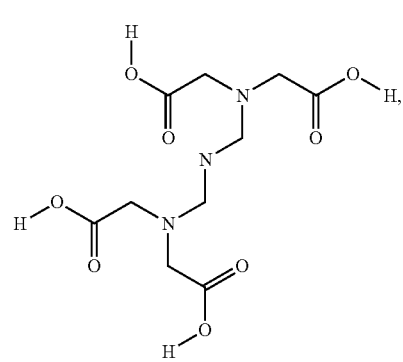
Formula (II-c)

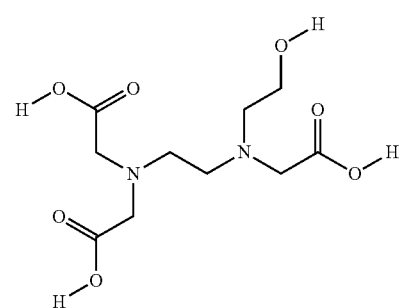
Formula (II-d)

Formula (II-e)

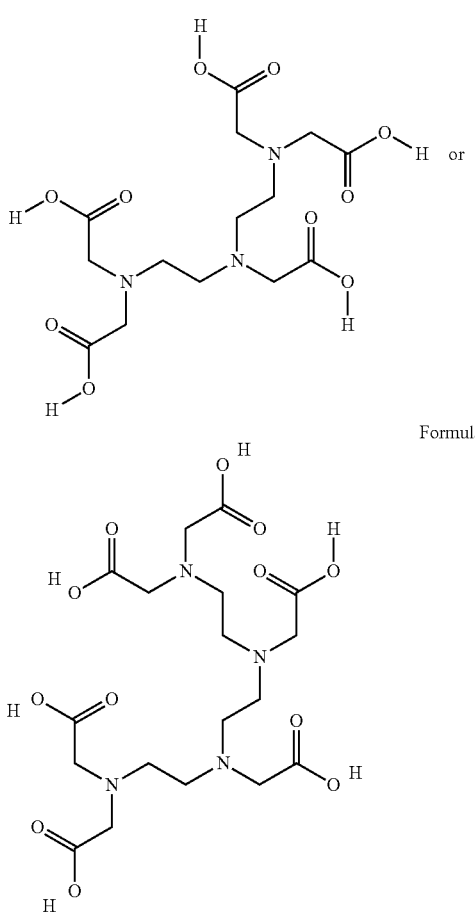

Formula (II-f)

In some embodiments, the aqueous medium is water.

In some embodiments, the composition further comprises an additive.

In another aspect, provided herein are adhesive compositions comprising a multivalent metal salt (e.g., tetracalcium phosphate), a compound of Formula (III), and an aqueous medium, wherein the compound of Formula (III) is:

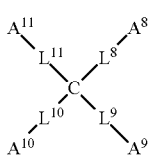

Formula (III)

wherein: each of $A^8$ and $A^9$ is independently selected from an acidic group (e.g., a carboxyl or phosphonyl); each of $A^{10}$ and $A^{11}$ is independently selected from an acidic group (e.g., a carboxyl or phosphonyl), a hydrogen atom, an alkyl, aryl, a hydroxy group, a thio group, and an amino group; each of $L^8$, $L^9$, $L^{10}$ and $L^{11}$ is independently bond, alkylene (e.g., $C_1$-$C_6$ alkylene), or heteroalkylene (e.g., $C_1$-$C_6$ heteroalkylene).

In some embodiments, $A^8$, $A^9$, and Aware carboxyl.

In some embodiments, $A^{10}$, $A^{11}$, are a hydrogen atom.

In some embodiments, $A^{11}$ is a hydroxy or amino group.

In some embodiments, $L^8$, $L^9$, $L^{10}$, and $L^{11}$ are a bond.

In some embodiments, $L^8$ and $L^9$ are $C_1$-$C_3$ alkylene.

In some embodiments $L^{11}$ is a heteroalkylene (e.g., $C_1$-$C_6$ heteroalkylene).

In some embodiments $L^{11}$ is methylenethiomethylene.

In some embodiments, the compound of Formula (III) comprises citric acid or malonic acid.

In some embodiments, the compound of Formula (III) is a compound of Formula (III-a), (III-b), (III-c), or (III-d):

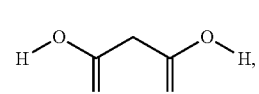

Formula (III-a)

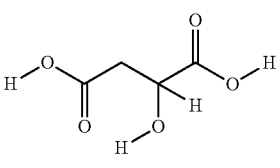

Formula (III-b)

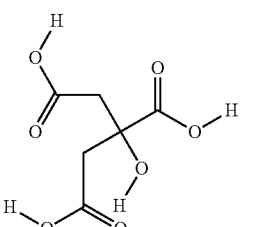

Formula (III-c)

or

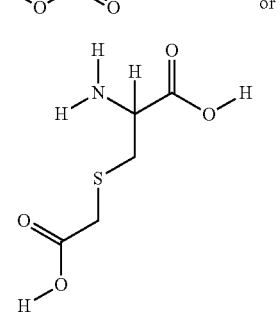

Formula (III-d)

In some embodiments, the aqueous medium is water.

In some embodiments, the composition further comprises an additive.

In yet another aspect, provided herein are adhesive compositions comprising a multivalent metal salt (e.g., tetracalcium phosphate), a compound of Formula (IV), and an aqueous medium, wherein the compound of Formula (IV) is:

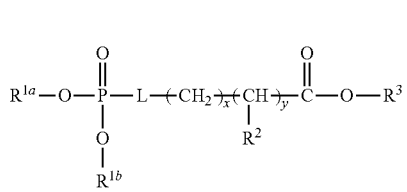

Formula (IV)

wherein: L is O, S, NH, or $CH_2$; each of $R^{1a}$ and $R^{1b}$ is independently H, an optionally substituted alkyl, or an optionally substituted aryl; $R^2$ is H, $NR^{4a}R^{4b}$, $C(O)R^5$, or $C(O)OR^5$; $R^3$ is H, an optionally substituted alkyl, or an optionally substituted aryl; each of $R^{4a}$ and $R^{4b}$ is independently H, $C(O)R^6$, or an optionally substituted alkyl; $R^5$ is H, an optionally substituted alkyl, or an optionally substituted aryl; $R^6$ is an optionally substituted alkyl or an optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O, and each of $R^{1a}$ and $R^{1b}$ is H.

In some embodiments, $R^2$ is selected from H, $NR^{4a}R^{4b}$, and $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H.

In some embodiments, L is O, each of Ria and Rib is independently H, $R^2$ is $NR^{4a}R^{4b}$, and each of $R^{4a}$ and $R^{4b}$ is independently H.

In some embodiments, $R^3$ is H. In some embodiments, L is O, each of $R^{1a}$ and $R^{1b}$ is independently H, $R^2$ is $NR^{4a}R^{4b}$, each of $R^{4a}$ and $R^{4b}$ is independently H, and $R^3$ is H.

In some embodiments, each of x and y is independently 0 or 1. In some embodiments, each of x and y is independently 1. In some embodiments, L is O, each of $R^{1a}$ and $R^{1b}$ is independently H, $R^2$ is $NR^{4a}R^{4b}$, each of $R^{4a}$ and $R^{4b}$ is independently H, $R^3$ is H, and each of x and y is 1.

In some embodiments, the compound of Formula (IV) is phosphoserine.

In some embodiments, the aqueous medium is water.

In some embodiments, the composition further comprises an additive. The additive may comprise a salt (e.g., calcium carbonate, calcium bicarbonate, sodium carbonate, sodium bicarbonate, sodium chloride, potassium chloride). The additive may comprise one or more of a filler, a formulation base, an abrasive (e.g., bone fragment), a coloring agent (e.g., dye, pigment, or opacifier), a flavoring agent (e.g., sweetener), or a polymer. The additive may comprise a viscosity modifier (e.g., a polyol (e.g., glycerol, mannitol, sorbitol, trehalose, lactose, glucose, fructose, or sucrose)). The additive may comprise a medication that acts locally (e.g., anesthetic, coagulant, clotting factor, chemotactic agent, and agent inducing phenotypic change in local cells or tissues), a medication that acts systemically (e.g., analgesic, anticoagulant, hormone, enzyme co-factor, vitamin, pain reliever, anti-inflammatory agent, chemotactic agent, or agent inducing phenotypic change in local cells or tissues), or an antimicrobial agent (e.g., antibacterial, antiviral, or antifungal agent).

In some embodiments, the compound is present in an amount from about 10% to about 90% weight by weight (w/w) of the total composition.

In some embodiment, the composition has a mean particle size of less than about 1.000 mm.

In some embodiments, the composition has a tacky state for up to 12 minutes after mixing with the aqueous medium. During the tacky state, the composition may have a tack stress in the range of about 10 kPa to about 250 kPa after mixing with the aqueous medium.

In some embodiments, the composition has a putty state for up to 15 minutes after mixing with the aqueous medium. During the putty state, the composition may have a tack stress in the range of about 10 kPa to about 250 kPa after mixing with the aqueous medium.

In some embodiments, the composition has an adhesive strength upon curing of greater than 100 kPa.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
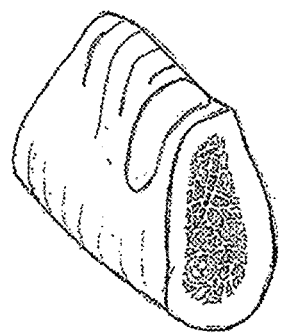
FIG. 1 is a schematic drawing of a gap, hole, or void on a surface.

Research aimed at addressing the intrinsic lack of strength of CPCs has produced formulations which include various fibers and polymeric chains within the mass of the set cement in order to provide better fracture toughness and tensile strength values. Various compositions of CPCs containing calcium phosphate salts, including octacalcium phosphate, calcium hydroxyapatite, tetra-calcium phosphate, dicalcium phosphate, α-tricalcium phosphate and/or β-tricalcium phosphate, also include polymers such as sodium alginate, chitosan, chondroitin sulfate, collagen, hyaluronic acid, hydroxypropylmethyl cellulose and methyl cellulose, methyl vinyl ether maleic acid copolymer, poly (2-hydroxyethyl methacrylate), and polyacrylic acid, for example, among either the solid or liquid components of the starting materials.

To improve injectability characteristics, CPCs may be refined, for example, in particle size distribution (particles may be smaller) or in particle shape (particles may be spherical). Formulations may be tuned in their liquid to powder ratio or formulated to reduce exclusion volume or plastic limit. Small amounts of poly(acrylic acid) or citrate ions may be added to formulations to decrease particle interactions, lowering viscosity. Small molecules such as glucose, chitosan, polycarboxylates, salicylates, and phosphoserine or structurally related amino acid phosphates may be included as a part of the CPC reaction mixture, for example, to improve characteristics such as setting kinetics, strength characteristics, biodegradability kinetics, etc.

The formulations disclosed herein, including those consisting primarily of tetra-calcium phosphate and phosphoserine, exhibit the advantageous property of robust adhesive behavior toward bone and other materials, including titanium.

The adhesive, self-setting compositions disclosed herein may feature an interaction between reagents which are electrically charged, but not purely anionic or purely cationic (e.g., zwitterion) and a mineral salt of a multivalent metal (e.g., tetra-calcium phosphate). Additionally, the interaction may be an acid base reaction resulting in the partial or complete consumption of the original mineral reagent, e.g., tetra-calcium phosphate, and the precipitation of a new distinct mineral phase, e.g., hydroxyapatite. The structure of the anionic components disclosed may also involve multiple nucleophilic groups which chelate or coordinate around the mineral multivalent metal subcomponents.

Provided herein are compositions comprising an acidic, or ionizing to anionic, component, with a mineral multivalent metal salt, which may result in the setting of the composition, for example, after mixing of the component reagents in an aqueous environment.

The interaction of the components of the composition may result in the production of a tacky and adhesive reaction mixture. In particular, the interaction may result in a viscous liquid which then solidifies forming a persistent bond to high-energy surfaces, e.g., bone, metal, glass, rock, etc. The adhesive bond interaction between the adhesive composition and the substrate surface may occur whether the substrate is dry or wet (e.g., dampened or submerged in an aqueous medium).

Chemical Definitions

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein.

"Alkyl" refers to a radical of a straight-chain or branched saturated hydrocarbon group. In some embodiments, an alkyl group has 1 to 3 carbon atoms ("$C_{1-3}$ alkyl"). In some embodiments, an alkyl group has 1 carbon atom ("$C_1$ alkyl"). Examples of $C_{1-6}$ alkyl groups include methyl ($C_1$) and propyl ($C_3$). Alkyl groups disclosed herein may be substituted or unsubstituted.

As used herein, "alkylene," refers to a divalent radical of an alkyl group. When a range or number of carbons is provided for a particular "alkylene" group, it is understood that the range or number refers to the range or number of carbons in the linear carbon divalent chain.

The term "heteroalkyl," as used herein, refers to an alkyl group, as defined herein, which further comprises 1 or more (e.g., 1 or 2) heteroatoms (e.g., non-ionizable heteroatoms, e.g., oxygen) within the parent chain, wherein the one or more heteroatoms is inserted between adjacent carbon atoms within the parent carbon chain and/or one or more heteroatoms is inserted between a carbon atom and the parent molecule, i.e., between the point of attachment.

As used herein, "alkylene," and "heteroalkylene," refer to a divalent radical of an alkyl and heteroalkyl group respectively. When a range or number of carbons is provided for a particular "alkylene" or "heteroalkylene" group, it is understood that the range or number refers to the range or number of carbons in the linear carbon divalent chain.

As used herein, "carboxyl" refers to —C(O)OH.

As used herein, "phosphonyl" refers to —P(O)(OH)$_2$.

As used herein, "aryl" refers to a functional group or substituent derived from an aromatic ring. In some embodiments, an aryl may be derived from an aromatic hydrocarbon. Exemplary aryl groups include, but are not limited to, phenyl, naphthyl, thienyl, indolyl, and xylyl. Aryl groups disclosed herein may be substituted or unsubstituted.

As used herein, "hydroxy" refers to —OH.

As used herein "thiol" refers to a sulfur analog of an alcohol. In some embodiments, a thiol group may include an organosulfur compound, for example, one that contains a carbon-bonded sulfhydryl. Exemplary thiol groups include —SH, —C—SH, and R—SH, where R represents an organic substituent, e.g. an aryl or alkyl.

As used herein "amino" refers to a compound that contains a nitrogen atom, for example, with a lone pair, attached to a hydrogen atom, alkyl group, or aryl group. In some embodiments, the amino may be derived from ammonia, for example, wherein one or more hydrogen atoms have been replaced by a substituent, for example an aryl or alkyl. The amino may be organic or inorganic. In some embodiments, an amino includes —NH$_2$, an amino acid, a biogenic amine, trimethylamine, and aniline.

Compositions

Provided herein are adhesive, self-setting compositions comprising a mixture of a multivalent metal salt, e.g., tetra-calcium phosphate, a compound of a Formula (e.g., Formula (I), Formula (II), Formula (III), Formula (IV), or a combination thereof), and an aqueous medium, e.g., water.

Exemplary multivalent metal salts may be organic or inorganic in nature and include calcium phosphates (e.g., hydroxyapatite, octacalcium phosphate, tetra-calcium phosphate, tricalcium phosphate), calcium nitrate, calcium citrate, calcium carbonate, magnesium phosphates, sodium silicates, lithium phosphates, titanium phosphates, strontium phosphates, barium phosphates, zinc phosphates, calcium oxide, magnesium oxide, and combinations thereof.

The amount of each multivalent metal salt (e.g., a calcium phosphate or calcium oxide or a combination thereof) may vary, e.g., between about 10% to about 90 weight by weight (w/w) of the total composition. In some embodiments, the amount of the multivalent metal salt (e.g., a calcium phosphate or calcium oxide or a combination thereof) is in the range of about 10% to about 90%, about 15% to about 85%, about 20% to about 80%, about 30% to about 75%, about 40% to about 70%, or about 50% to about 65% w/w of the total composition. In other embodiments, the amount of the metal salt (e.g., a calcium phosphate or calcium oxide or a combination thereof) is in the range of about 5% to about 95%, about 10% to about 85%, about 15% to about 75%, about 20% to about 65%, about 25% to about 55%, or about 35% to about 50% w/w of the total composition.

In some embodiments, the multivalent metal salt comprises one or more alkaline earth metals, e.g., beryllium, magnesium, barium, radium, strontium, or calcium. In some embodiments, the multivalent metal salt may comprise a mixed salt of several metal ions, e.g., a mixed salt of alkali earth metal ions. In some embodiments, the multivalent metal salt comprises calcium. In some embodiments, the multivalent metal salt comprises calcium and phosphate. In some embodiments, the multivalent metal salt comprises tetra-calcium phosphate. In some embodiments, the composition comprises a plurality of multivalent metal salt compounds. In some embodiments, the plurality comprises tetra-calcium phosphate and at least one other multivalent metal salt compound. In some embodiments, the multivalent metal salt comprises hydroxyapatite. In some embodiments, the multivalent metal salts comprise tricalcium phosphate. In some embodiments, the tricalcium phosphate comprises either alpha tricalcium phosphate or beta tricalcium phosphate. In some embodiments, the multivalent metal salts comprise an oxide. In some embodiments, the multivalent metal salt is calcium oxide. In some embodiments, the multivalent metal salt compound does not comprise tetra-calcium phosphate. In some embodiments, the composition comprises tricalcium phosphate and calcium oxide.

In some embodiments, the multivalent metal salt is initially provided as a powder or as a granule. These powders may exhibit a mean particle size of about 0.001 to about 1.000 mm, about 0.001 to about 0.250 mm, about 0.005 to about 0.150 mm, about 0.250 to about 0.750 mm, 0.25 to about 0.50 mm, 0.10 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The powder may have a mean particle size of less than about 1.000 mm. The particle size distribution may be multi-modal to include any combination of mean particle sizes as previously described. These granules may exhibit a mean granule size of about 0.050 mm to about 5 mm, about 0.100 mm to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The granule size distribution may be multi-modal to include any combination of mean granule sizes as previously described. The granules may be supplied with a various proportion of porosity and a various size of internal pores. The pores may communicate with each other. The pores may communicate with granule surface. In some embodiments, the pores do not communicate with each other. In some embodiments, the pores do not communicate with granule surface. In some embodiments, varying sizes of said powders or granules may be used in the adhesive composition.

In the present disclosure, the multivalent metal salts (e.g., tetra-calcium phosphate) may react with a compound of a Formula (e.g., Formula (I), Formula (II), Formula (III), Formula (IV), or a combination thereof to form an adhesive composition when combined with an aqueous medium.

In some embodiments, the aqueous medium comprises water (e.g., sterile water), saliva, buffers (e.g., sodium phosphate, potassium phosphate, or saline (e.g., phosphate buffered saline)), blood, blood-based solutions (e.g., plasma, serum, bone marrow), spinal fluid, dental pulp, cell-based solutions (e.g., solutions comprising fibroblasts, osteoblasts, platelets, odontoblasts, stem cells (e.g., mesenchymal stem cells) histiocytes, macrophages, mast cells, or plasma cells), or combinations thereof in the form of aqueous solutions, suspensions, and colloids. In some embodiments, the aqueous medium comprises sterile water, distilled water, deionized water, sea water, or fresh water.

In some embodiments, the aqueous medium comprises water from the environment, e.g., fresh water, salt water or brackish water from the oceans, seas, bays, rivers, streams, ponds or other moving or standing water sources.

Compounds

Compositions disclosed herein may comprise a small molecule anionic reactant and a mineral salt of a multivalent metal, for example, in an aqueous medium. The small molecule anionic reactant may comprise a compound of a Formula (e.g., Formula (I), Formula (II), Formula (III), or Formula (IV)) or combinations thereof.

Compositions disclosed herein may comprise a compound of Formula (I):

Formula (I)

wherein: each of $A^1$, $A^2$, and $A^3$ is independently selected from an acidic group (e.g., a carboxyl or phosphonyl); and each of $L^1$, $L^2$, and $L^3$ is independently bond, alkylene (e.g., $C_1$-$C_6$ alkylene), or heteroalkylene (e.g., $C_1$-$C_6$ heteroalkylene).

In some embodiments, each of $A^1$, $A^2$, and $A^3$ is independently a carboxyl or phosphonyl. In some embodiments, $A^1$ is carboxyl, and $A^2$ and $A^3$ are phosphonyl. In some embodiments, $A^1$, $A^2$ and $A^3$ are phosphonyl.

In some embodiments, each of $L^1$, $L^2$, and $L^3$ is $C_1$-$C_3$ alkylene. In some embodiments, each of $L^1$, $L^2$, and $L^3$ is $C_1$ alkylene.

In some embodiments, the compound of Formula (I) is a compound of Formula (I-a) or (I-b):

Formula (I-a)

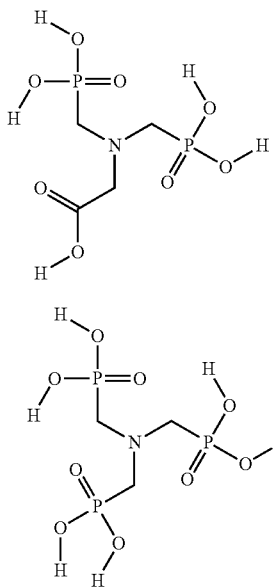

or

Formula (I-b)

In some embodiments, the aqueous medium is water.

In some embodiments, the composition further comprises an additive.

Compositions disclosed herein may comprise a compound of Formula (II):

Formula (II)

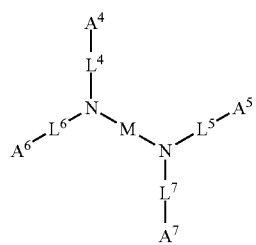

wherein: each of $A^4$, $A^5$, and $A^6$, is independently selected from an acidic group (e.g., a carboxyl or phosphonyl); $A^7$ is selected from an acidic group (e.g., a carboxyl or phosphonyl), a hydrogen atom, an alkyl, an aryl, a hydroxy group, a thio group, and an amino group; each of $L^4$, $L^5$, $L^6$, and $L^7$ is independently bond, alkylene (e.g., $C_1$-$C_6$ alkylene), or heteroalkylene (e.g., $C_1$-$C_6$ heteroalkylene); and M is alkylene (e.g., $C_1$-$C_6$ alkylene) or heteroalkylene (e.g., $C_1$-$C_6$ heteroalkylene).

In some embodiments, $A^4$, $A^5$, $A^6$ and $A^7$ are carboxyl.

In some embodiments, $L^4$, $L^5$, $L^6$, and $L^7$ are $C_1$-$C_3$ alkylene. In some embodiments, $L^4$, $L^5$, $L^6$, and $L^7$ are $C_1$ alkylene.

In some embodiments, M is $C_1$-$C_4$ alkylene. In some embodiments, M is $C_2$ alkylene. In some embodiments, M is $C_3$ alkylene. In some embodiments, M is $C_1$-$C_6$ heteroalkylene. In some embodiments, M is $C_6$ heteroalkylene. In some embodiments, M is bis(ethyleneoxy)ethylene. In some embodiments, M includes side chains. In some embodiments, M includes multiple side chains. In some embodiments, M includes one or multiple carboxymethylene side chains. In some embodiments, M includes one or multiple N-carboxymethylene groups or N-hydroxymethylene groups.

In some embodiments, the compound of Formula (II) includes three, four, five, six, or more N-carboxymethylene groups.

In some embodiments, the compound of Formula (II) is a compound of Formula (II-a), (II-b), (II-c), (II-d), (II-e), or (II-f):

Formula (II-a)

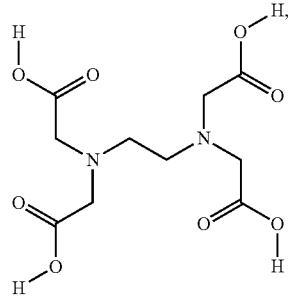

Formula (II-b)

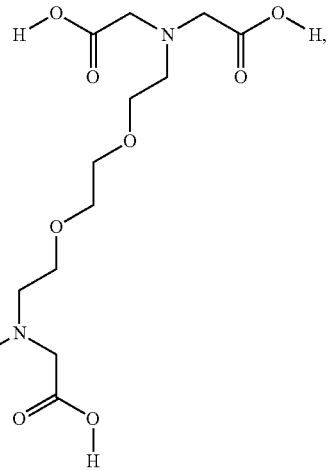

Formula (II-c)

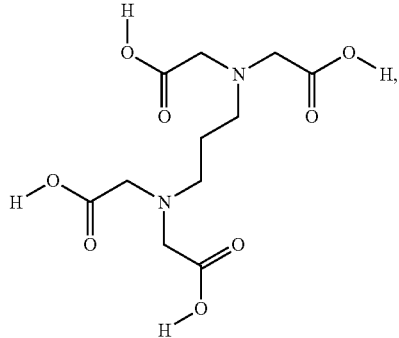

-continued

Formula (II-d)

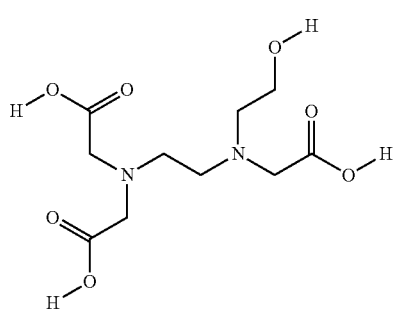

Formula (II-e)

Formula (II-f)

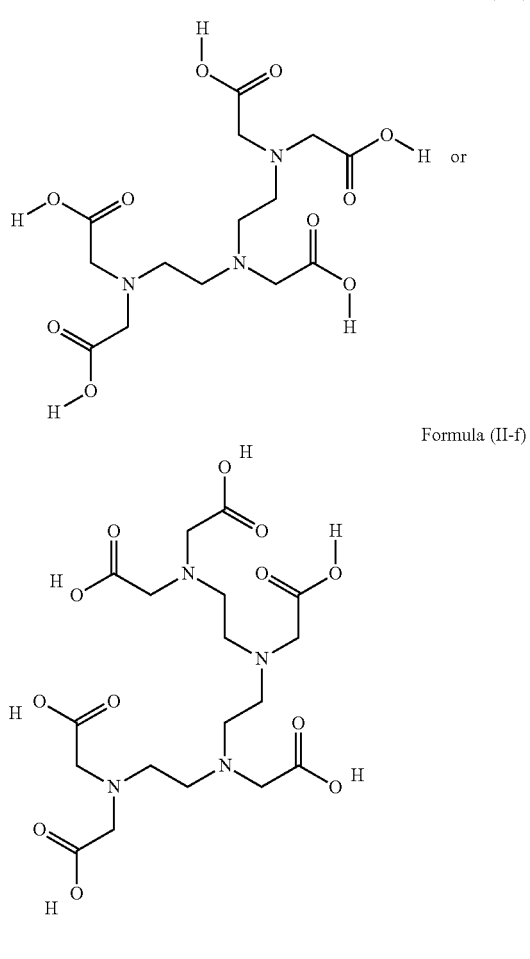

In some embodiments, the aqueous medium is water.

In some embodiments, the composition further comprises an additive.

Compositions disclosed herein may comprise a compound of Formula (III):

Formula (III)

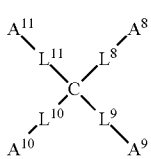

wherein: each of $A^8$ and $A^9$ is independently selected from an acidic group (e.g., a carboxyl or phosphonyl); each of $A^{10}$ and $A^{11}$ is independently selected from an acidic group (e.g., a carboxyl or phosphonyl), a hydrogen atom, an alkyl, aryl, a hydroxy group, a thio group, and an amino group; each of $L^8$, $L^9$, $L^{10}$ and $L^{11}$ is independently bond, alkylene (e.g., $C_1$-$C_6$ alkylene), or heteroalkylene (e.g., $C_1$-$C_6$ heteroalkylene.

In some embodiments, $A^8$, $A^9$, and $A^{10}$ are carboxyl.

In some embodiments, $A^{10}$, $A^{11}$, are a hydrogen atom.

In some embodiments, $A^{11}$ is a hydroxy or amino group.

In some embodiments, $L^8$, $L^9$, $L^{10}$, and $L^{11}$ are a bond.

In some embodiments, $L^8$ and $L^9$ are $C_1$-$C_3$ alkylene.

In some embodiments $L^{11}$ is a heteroalkylene (e.g., $C_1$-$C_6$ heteroalkylene).

In some embodiments $L^{11}$ is methylenethiomethylene.

In some embodiments, the compound of Formula (III) is a compound of Formula (III-a), (III-b), (III-c), or (III-d):

Formula (III-a)

Formula (III-b)

Formula (III-c)

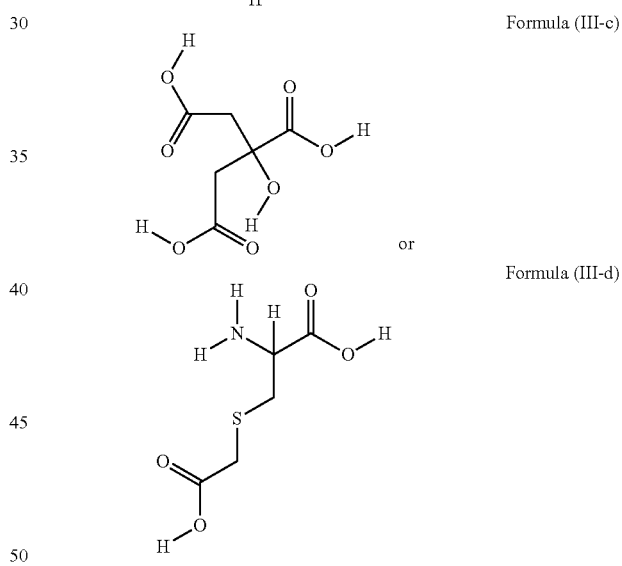

or

Formula (III-d)

In some embodiments, the aqueous medium is water.

In some embodiments, the composition further comprises an additive.

Compositions disclosed herein may comprise a compound of Formula (IV):

Formula (IV)

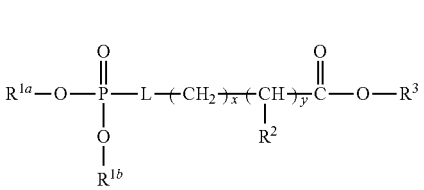

wherein: L is O, S, NH, or CH$_2$; each of R$^{1a}$ and R$^{1b}$ is independently H, an optionally substituted alkyl, or an optionally substituted aryl; R$^2$ is H, NR$^{4a}$R$^{4b}$, C(O)R$^5$, or C(O)OR$^5$; R$^3$ is H, an optionally substituted alkyl, or an optionally substituted aryl; each of R$^{4a}$ and R$^{4b}$ is independently H, C(O)R$^6$, or an optionally substituted alkyl; R$^5$ is H, an optionally substituted alkyl, or an optionally substituted aryl; R$^6$ is an optionally substituted alkyl or an optionally substituted aryl; and each of x and y is independently 0, 1, 2, or 3.

In some embodiments, L is O or S. In some embodiments, L is O. In some embodiments, each of R$^{1a}$ and R$^{1b}$ is independently H. In some embodiments, L is O, and each of R$^{1a}$ and R$^{1b}$ is H.

In some embodiments, R$^2$ is selected from H, NR$^{4a}$R$^{4b}$, and C(O)R$^5$. In some embodiments, R$^2$ is NR$^{4a}$R$^{4b}$. In some embodiments, R$^2$ is NR$^{4a}$R$^{4b}$ and each of R$^{4a}$ and R$^{4b}$ is independently H.

In some embodiments, L is O, each of Ria and Rib is independently H, R$^2$ is NR$^{4a}$R$^{4b}$, and each of R$^{4a}$ and R$^{4b}$ is independently H.

In some embodiments, R$^3$ is H. In some embodiments, L is O, each of R$^{1a}$ and R$^{1b}$ is independently H, R$^2$ is NR$^{4a}$R$^{4b}$, each of R$^{4a}$ and R$^{4b}$ is independently H, and R$^3$ is H.

In some embodiments, each of x and y is independently 0 or 1. In some embodiments, each of x and y is independently 1. In some embodiments, L is O, each of R$^{1a}$ and R$^{1b}$ is independently H, R$^2$ is NR$^{4a}$R$^{4b}$, each of R$^{4a}$ and R$^{4b}$ is independently H, R$^3$ is H, and each of x and y is 1.

In some embodiments, the compound of Formula (IV) is phosphoserine.

In some embodiments, the aqueous medium is water.

In some embodiments, the composition further comprises an additive.

The amount of compound of a Formula (i.e., Formula (I), Formula (II), Formula (III), or Formula (IV), or a combination thereof) may vary, e.g., between about 10% to about 90% weight by weight (w/w) of the total composition. In some embodiments, the amount of compound of a Formula (i.e., Formula (I), Formula (II), Formula (III), or Formula (IV), or a combination thereof) is in the range of about 10% to about 90%, about 15% to about 85%, about 20% to about 80%, about 30% to about 75%, about 40% to about 70%, or about 50% to about 65% w/w of the total composition. In other embodiments, the amount of compound of a Formula (i.e., Formula (I), Formula (II), Formula (III), or Formula (IV), or a combination thereof) is in the range of about 5% to about 95%, about 10% to about 85%, about 15% to about 75%, about 20% to about 65%, about 25% to about 55%, or about 35% to about 50% w/w of the total composition.

In some embodiments, the compound is initially provided as a powder or as a granule. These powders may exhibit a mean particle size of about 0.001 to about 1.000 mm, about 0.001 to about 0.250 mm, about 0.005 to about 0.150 mm, about 0.250 to about 0.750 mm, 0.25 to about 0.50 mm, 0.10 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The powder may have a mean particle size of less than about 1.000 mm. The particle size distribution may be multi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The granule size may be multi-modal to include any combination of mean granule sizes as previously described. The granules may be supplied with a various proportion of porosity and a various size of internal pores. The pores may communicate with granule surface or not. In some embodiments, varying sizes of said powders or granules may be used in the adhesive composition.

Additives

In some embodiments, the compositions may further comprise an additive. An additive may be used to impart additional functionality to the composition of the disclosure, such as improving or affecting the handling, texture, durability, strength, or resorption rate of the material, or to provide additional cosmetic or medical properties. Exemplary additives may include salts (e.g., calcium carbonate, calcium bicarbonate, sodium carbonate, sodium bicarbonate, sodium chloride, potassium chloride), fillers, formulation bases, viscosity modifiers (e.g., polyols (e.g., glycerol, mannitol, sorbitol, trehalose, lactose, glucose, fructose, or sucrose)), abrasives (e.g., bone fragments), coloring agents (e.g., dyes, pigments, or opacifiers), flavoring agents (e.g., sweeteners), medications that act locally (e.g., anesthetics, coagulants, clotting factors, chemotactic agents, and agents inducing phenotypic change in local cells or tissues), medications that act systemically (e.g., analgesics, anticoagulants, hormones, enzyme co-factors, vitamins, pain relievers, anti-inflammatory agents, chemotactic agents, or agents inducing phenotypic change in local cells or tissues), antimicrobial agents (e.g., antibacterial, antiviral, or antifungal agents) or combinations thereof. In some embodiments, the additive comprises a polymer. The biologically active substances (e.g., medicines) in the categories above might include active substances or precursors, which become biologically active upon modification after interaction with the surrounding environment. The substances might be synthetic, semisynthetic, or biologically derived (e.g., peptides, proteins, or small molecules). The substances might include, but not be limited to anti-inflammatories (e.g., steroids, nonsteroidal anti-inflammatory drugs, cyclooxygenase inhibitors), complement proteins, bone morphogenic factors and proteins, hormones active locally or systemically (e.g., parathyroid hormone, calcitonin), or other small molecules (e.g., calciferols).

In some embodiments, the additive is a polymer. Suitable polymers incorporated as additives into the adhesive composition may contain functional groups that contains electronegative atoms as the bonding sites of the polymer surfaces to the available metal ions, such as electronegative carbonyl oxygen atom(s) of the ester group or electronegative nitrogen atom(s) of the amine group as the bonding sites of the polymer surfaces to the available metal ions. These functional groups can be either in the backbone chain of the polymer or in groups pendant to the polymer chain. These polymeric based compounds may include, but are not limited to, one or more of the following; poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(lactide-co-glycolide), poly(glycolide-co-trimethylene carbonate), poly(glycolide-co-caprolactone), poly(glycolide-co-dioxanone-co-trimethylene-carbonate), poly(tetramethylglycolic-acid-co-dioxanone-co-trimethylenecarbonate), poly(glycolide-co-caprolactone-co-lactide-co-trimethylene-carbonate), poly(hydroxybutyrate-co-hydroxyvalerate), poly(methylmethacrylate), poly(acrylate), polyamines, polyamides, polyimidazoles, poly(vinyl-pyrrolidone), collagen, silk, chitosan, hyaluronic acid, gelatin and/or mixtures thereof. In addition, copolymers of the above homopolymers also can be used.

The general structural nature of a polymer (e.g., a polymer used as an additive in an adhesive composition described herein) may include a linear homo and copolymer, a cross linked polymer, a block polymer, a branched polymer, a hyper branched polymer, or a star shaped polymer. The polymers can be added to the formulation in the form of a solution, powder, fiber, resin, liquid crystal, hydrogel, chip, flake, granule, and the like. The polymeric material can be included directly within the adhesive composition or can be an adjunct that is applied in situ as the cement is applied to the bone.

In some embodiments, the composition comprises a plurality of said additives. In some embodiments, certain additives may be provided as powders or granules or solutes or any combination thereof. These powders may exhibit a mean particle size of about 0.001 to about 1.000 mm, about 0.001 to about 0.250 mm, about 0.005 to about 0.150 mm, about 0.250 to about 0.750 mm, 0.25 to about 0.50 mm, 0.10 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The powder may have a mean particle size of less than about 1.000 mm. The particle size distribution may be multi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The granule size distribution may be multi-modal to include any combination of mean granule sizes as previously described. The granules may be supplied with a various proportion of porosity and a various size of internal pores. The pores may communicate with granule surface. In some embodiments, the pores do not communicate with granule surface. In some embodiments, varying sizes of said powders or granules may be used in the adhesive composition.

In some embodiments, certain additives may be provided as fibers. In some embodiments, the fibers may exhibit a mean fiber diameter of about 0.010 mm to about 2 mm, about 0.010 mm to about 0.50 mm, or about 0.025 mm to about 0.075 mm. These fibers may exhibit a mean fiber length of about 0.025 mm to about 50.0 mm, about 0.50 mm to 10 mm, or about 1.00 mm to about 3.50 mm. The fiber diameter distribution or length distribution may be multi-modal to include any combination of mean fiber diameter or length.

Properties

The adhesive compositions described herein might be applied to the surface of a structure in its fluid or semi-solid state by means of an injection delivery device or by application using an instrument such as a spatula. The viscosity of the adhesive composition when in its fluid state might be as low as about 100 cP to about 10,000 cP and when it reaches its semi-solid state from about 10,000 cP to about 250,000 cP. The viscosity and cohesion properties of the adhesive composition will facilitate the ability to squeeze the material through a needle or cannula as small as 18 gauge when the viscosity is in the low range of its fluid state. With viscosities in the semi-solid state, the shape and amount of material can be altered through spreading or removal techniques without substantially effecting the strength of the set material. In some embodiments, the working time of the adhesive composition is when the viscosity is between about 100 cP to about 250,000 cP.

The adhesive compositions described herein may have a tacky state after mixing with an aqueous medium. This tacky property is retained for a number of days (e.g., up to 7 days, up to 3 days, up to 1 day), up to hours (e.g., up to 12 hours, up to 4 hours, up to 1 hour), up to minutes (e.g., up to 30 minutes, up to 12 minutes, up to about 4 minutes, up to about 2 minutes, up to about 1 minute), or seconds (e.g., up to 30 seconds, up to 5 seconds, up to 2 seconds), after mixing with the aqueous medium. The time of the tacky state may be dependent on a number of factors including relative ratio of the components, the particle sizes of the component materials, the presence of additives and the like, or the temperature of the environment. During the tacky state, the adhesive compositions will adhere to surfaces, optionally without the need for external clamping or other application of pressure. In the tacky state, the compositions will adhere bone to bone and bone to other materials. In the tacky state, the compositions may adhere materials such as stainless steel, titanium, zirconia, polyether ether ketone, steel, aluminum, copper, brass, aragonite, calcite, cement, alumina, concrete, ceramics, rock, glass, and other metals or substances. During the tacky state the contacting surfaces may be held together by the adhesive composition itself, without the need for external force, until the composition sets to the final hardened cement state. The tacky state can allow the materials to be positioned or repositioned without appreciable loss of cured strength.

The amount of force needed to remove two adherent pieces of material from each other during the tacky state is the tack strength. For the adhesive composition as described herein, these adhesive compositions when applied to join or affix two surfaces may have a tack stress as measured by tensile or shear loads during the tacky state, from about 10 kPa to about 250 kPa and preferably from about 50 kPa to about 150 kPa. The tack stress may be sufficiently high that the items to be joined need not be held or clamped together unless there is an opposing strength of the items greater than the tack strength. During the tacky state the materials may be positioned, repositioned or reopposed several times without appreciable loss of cured adhesive strength.

In some embodiments, the adhesive compositions may adopt a pliable working or putty state after mixing with an aqueous medium prior to hardening, which is present for up to about one week or less, one day or less, one hour or less, 30 minutes or less, depending on the components of said compositions and the conditions of the application, e.g., temperature. In some embodiments, the adhesive compositions may adopt a pliable working or putty state for less than or equal to about one week after mixing with an aqueous solution or suspension, e.g., less than about six days, less than about five days, less than about four days, less than about three days, less than about two days, less than about one day, less than about twelve hours, less than about one hour, less than about 30 minutes, less than about 20 minutes, less than about 15 minutes, less than about 10 minutes, less than about 5 minutes, less than about 3 minutes, less than about 2 minutes, less than about 1 minute, less than about 30 seconds, less than about 5 seconds after mixing with an aqueous solution or suspension.

During the putty state, which follows the tacky state, the adhesive compositions can be shaped or sculpted, for example, to fill voids in bone or acquire a desired contour, size or form. The combined time of the tacky state and the putty state is referred to herein as working time. Typical compositions may have a working time of up to at least 3 minutes, up to at least 5 minutes, up to at least 8 minutes, up to at least 12 minutes, or up to at least 15 minutes from initial mixing, after which time the compositions have sufficiently begun hardening.

In some embodiments, after a set amount of time, the adhesive compositions may adopt a hard, cement-like state. This process of conversion from the pliable working state to the cement-like state may be referred to as "hardening," "curing," or "setting." The adhesive compositions may harden, cure, or set such that the materials that have been affixed to each other with the adhesive compositions cannot be separated without the application of significant force. The compositions typically will begin to harden within about 8 minutes, e.g., within about 5 minutes, within about 3 minutes, or within about 15 minutes, after mixing with the aqueous medium near room or body temperature. Compositions may be formulated to harden within a specific amount of time. For example, certain formulations may harden within less than 8 minutes, e.g., less than 30 seconds. Other formulations may harden within more than 8 minutes, for example, more than about 12 minutes, more than about 15 minutes, more than one day or about one week. The variance in hardening times may be due to the composition or the environment (e.g., temperature). In some embodiments, hardening time may range between less than 30 seconds to more than one day, under the same external conditions. The described tacky, putty, and set state occur in a wet environment or dry environment.

In some embodiments, the adhesive compositions may exhibit an adhesive strength in the cement-like state in the range of about 100 kPa to about 12,000 kPa, depending on the application and the particular components and ratios of components in said adhesive compositions. In some embodiments, the adhesive strength of the adhesive compositions in the cement-like state is between about 100 kPa and e.g., about 10,000 kPa, about 9,000 kPa, about 8,000 kPa, about 7,000 kPa, about 6,000 kPa, about 5,000 kPa, about 4,000 kPa, about 3,000 kPa, about 2,000 kPa, about 1,000 kPa, about 750 kPa, about 500 kPa, about 250 kPa, or about 200 kPa. In some embodiments, the adhesive strength of the adhesive compositions in the cement-like state is between about 100 kPa, about 200 kPa, about 300 kPa, about 400 kPa, about 500 kPa, about 600 kPa, about 700 kPa, about 800 kPa, about 900 kPa, about 1,000 kPa, about 2,500 kPa, about 5,000 kPa, about 7,500 kPa, about 10,000 kPa or about 12,000 kPa. In some embodiments, the adhesive strength of the adhesive compositions in the cement-like state is in the range of about 200 kPa and about 2,500 kPa. In some embodiments, the adhesive strength of the adhesive compositions in the cement-like state is greater than 100 kPa.

In some embodiments, the particular components of the adhesive compositions may be selected to achieve the desired strength depending on the intended use of the adhesive compositions. In all embodiments, a skilled practitioner (e.g., a doctor, dentist, surgeon, nurse, medic, emergency technician, carpenter, mechanic, plumber, or other suitable person) may alter the specific components to achieve the desired adhesive properties of said composition based on the intended use or desired outcome.

The adhesive compositions described herein may be applied to surfaces that are dry, immersed in, submerged in, or damp with an aqueous medium (e.g., fresh water, saline, blood, sea water), or condensing water.

Medical Uses of the Adhesive Compositions

The adhesive compositions may be useful in a wide variety of applications, for example, medical applications. In some embodiments, the adhesive compositions may be used to adhere a structure to a surface (e.g., a bone, a tooth, or another structure, e.g., as shown in FIGS. 1-20). In some embodiments, the structure comprises an implant, anchor, graft, device, biological tissue, prosthetic device, dental crown, or another bone or bone fragment. In some embodiments, the surface is the endosseous surface or the subperiosteal surface of the bone. In some embodiments, the adhesion of said structure is temporary, such that said structure is removed after a period of time (e.g., greater than about 1 hour, about 2 hours, about 12 hours, about 24 hours, about 1 week, about 1 month, about 6 months, about 1 year, about 5 years). In other embodiments, the adhesion of said structure is permanent or intended to be permanent or until the material is resorbed and replaced with bone.

Figure 2:
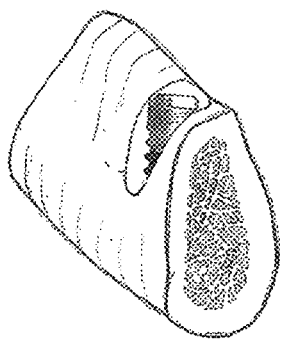
FIG. 2 is a schematic drawing of a structure placed within the gap, hole, or void shown in FIG. 1.
Figure 3:
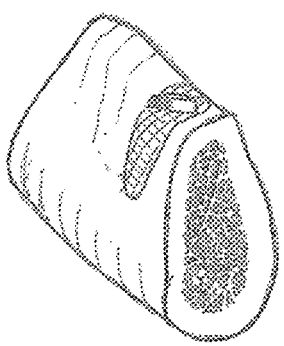
FIG. 3 is a schematic drawing of an adhesive composition used to fill a gap, hole, or void on a surface after placement of a structure, as shown in FIGS. 1 and 2, according to an embodiment disclosed herein.
Figure 17:
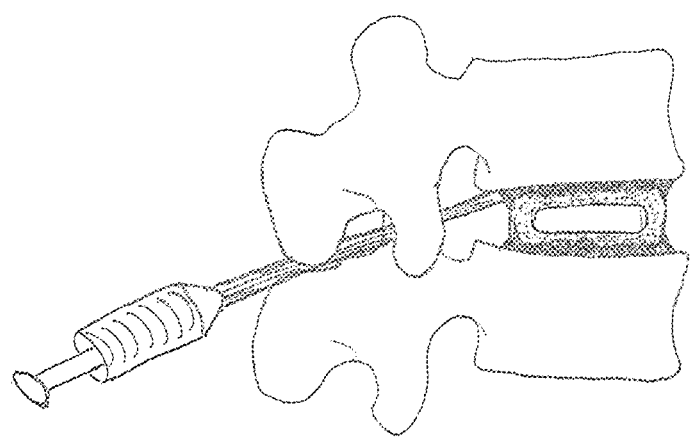
FIG. 17 is an alternate schematic drawing of an adhesive composition being delivered to an application site via injection, according to an embodiment disclosed herein.

In other embodiments, the adhesive compositions may be used to fill a gap, hole, or void in a surface either before (e.g., a bone or other structure, e.g., as shown in FIGS. 4-15) or after placement of a structure into or onto a surface (e.g., implant, anchor, graft, device, biological tissue, or another bone or bone fragment, e.g., as shown in FIGS. 1-3). It is envisioned that this particular application may be useful when the core diameter of the gap, hole, or void is larger than the size of the structure, for instance, in the placement of a dental implant into the alveolar ridge (e.g., as shown in FIGS. 1-3). In this instance, the adhesive composition may impart additional strength, fixation, stability, durability, or other advantageous property to the attached structure at the attachment site. In other embodiments, the adhesive composition may impart fixative strength to the attached structure at the attachment site (e.g., as shown in FIG. 17). In some embodiments, the adhesive compositions may support new bone growth at the attachment site, e.g., by increasing or stimulating the bone resorption, deposition, or the remodeling rate. In additional embodiments, the adhesive compositions may be used to fill gaps created in or at the attachment site to create a seal (e.g., as shown in FIGS. 1-3 and FIG. 22), prevent leakage, or prevent microbial growth (e.g., an infection), or prevent fibrous tissue ingress. In some embodiments, the adhesive compositions may be used to prevent microbial ingress, e.g., to prevent an infection, e.g., to prevent fibrous tissue ingress (e.g., as shown in FIGS. 1-3 and FIG. 22).

In some embodiments, the adhesive compositions are used during a medical procedure. In some embodiments, the adhesive compositions are used during a surgical or dental procedure. In some embodiments, said medical procedure comprises a surgery (e.g., dental surgery, sinus surgery, facial surgery, or other surgery to the skeletal region). In other embodiments, the medical procedure comprises a spinal fusion, prosthetic limb attachment, skeletal cosmetic augmentation, filling of a defect, a void, or a deficiency, or other surgery to the musculoskeletal system. The surgical procedures may be through open tissue procedures to expose or gain access to the application site. Likewise, the surgical procedures may be through small incisions or through minimally invasive approaches in order to minimize tissue damage (e.g., with needle access to an application site and to inject an exemplary composition during spinal fusion procedures as shown in FIGS. 16-20). Such surgical procedures could be performed in sterile operating rooms or in non-sterile settings such as at a clinic, office setting, or at a remote site outside a hospital setting (e.g., injury site, battlefield, ocean, ambulance).

In some embodiments, the compositions may be used in a dental application (e.g., ridge preservation graft following tooth extraction, filling of a cavity or defect resulting from tooth decay, fracture, attrition, abrasion, erosion, abfraction, placement of a dental implant or device, osteoperiosteal graft, endodontic reconstruction, or others). In some embodiments, the compositions are used as an onlay graft to increase bone volume (e.g., as shown in FIGS. 4-16 and FIG. 18). In other embodiments, the adhesive compositions may be used in ossicular chain reconstruction or to adhere a structure to the inner ear or middle ear, e.g., a hearing aid. In other embodiments, the adhesive compositions may be used to provide contour in a surgical application, e.g., for facial bone augmentation applications. In some embodiments, the adhesive compositions may be used in a cosmetic application.

In other embodiments, compositions are placed by injection into an extraction socket and allowed to become solid. The solid material is allowed to remain undisturbed until the composition hardens, cures, or resorption of the material proceeds, resulting in increased bone volume through alveolar fill graft and ridge preservation.

In other embodiments, the adhesive compositions are placed or injected into a bone void resulting from the removal of a bone cyst, or granuloma, or similar bone defect crestal, central, or lateral to the alveolar ridge (e.g., bone) or another portion of the facial skeleton, and allowed to become solid. The solid material is allowed to remain undisturbed until the resorption of the material proceeds, resulting in increased bone strength and restoration of the bone contour.

In other embodiments, the adhesive compositions are placed or injected into a bone void partially or totally surrounding the superficial aspect of a structure (e.g., an implant) as it emerges from the bone, thereby providing continuous contour to the surface of the bone, augments the stability of the structure (e.g., implant) in the bone if needed, and excludes fibrous tissue cells from the void. In some embodiments, the adhesive compositions are placed or injected into a bone void partially or totally surrounding the superficial aspect of a structure to seal a gap to exclude fibrous tissue or prevent microbial ingress (e.g., prevent an infection, e.g., as shown in FIGS. 1-3 and FIG. 22). In some embodiments, this might be performed during an initial visit after an implant is placed. In other embodiments, this might be performed during a rescue procedure of an implant.

In other embodiments, the adhesive compositions are placed or injected into a prepared extraction socket, or a similar bone void, and a structure (e.g., an implant) is placed into this preparation in desired relationship to the surroundings before the composition becomes solid. Once the composition becomes solid, the structure (e.g., an implant) possesses primary stability, in some embodiments may mean that the implant body is clinically immobile relative the bone host site in lateral and axial load, and in torsional load of at least 10 Ncm (e.g., 15 Ncm) of clockwise or counterclockwise rotation. In some embodiments, primary stability may mean that the implant body is clinically immobile relative the bone host site when using a Ostell meter that uses Resonance Frequency Analysis with an ISQ value measured, wherein the ISQ scale is normalized from 0-100, wherein the higher the ISQ the more stable the implant, and/or wherein an ISQ value>50 has been clinically accepted to indicate the implant is sufficiently stable to allow for loading. In other embodiments, primary stability refers to the relative immobility of the adhered surfaces that persist when the adhesive bond is subjected to load-bearing stress of at least 250 kPa.

The placement of endosseous structures might be performed through open procedures involving partial or full thickness flap reflection or performed through flapless procedures with minimal periosteal reflection (e.g., punch access, laser, electro cautery, direct drilling, etc.).

The placement of the adhesive composition in contact with bone might be performed through open procedures involving partial or full thickness flap reflection or performed through flapless procedures with minimal soft tissue incision or interruption (e.g., injection through cannula or needle following a tunneling approach to gain access).

The adhesive composition might be applied to the surface of a structure in its fluid or semi-solid state by means of an injection delivery device or by application using an instrument such as a spatula. The viscosity of the adhesive composition when in its fluid state might be as low as about 100 cP to about 10,000 cP and when it reaches its semi-solid state from about 10,000 cP to about 250,000 cP. The viscosity and cohesion properties of the adhesive composition will facilitate the ability to squeeze the material through a needle or cannula as small as 18 gauge when the viscosity is in the low range of its fluid state. With viscosities in the semi-solid state, the shape and amount of material can be altered through spreading or removal techniques without substantially effecting the strength of the set material. In some embodiments, the working time of the adhesive composition is when the viscosity is between about 100 cP to about 250,000 cP.

The adhesive composition might be applied to a surface of a host structure in its fluid or semi-solid state and remain in these states during the subsequent placement of another structure in contact with the adhesive composition before the adhesive composition hardens to a solid, whereupon the structure possesses primary stability.

The adhesion of structures to a host structure might be performed into a bed, mantle, or layer of the adhesive composition that surrounds, contacts, or embeds the structure while the adhesive composition is in a fluid or semi-solid state prior to hardening, whereupon the structure possesses primary stability (e.g., as shown in FIGS. 1-3, 13-15, and 21-22). To do so, the host site for the structure may first require a preparation prior to application of the adhesive composition. The adhesive composition may be applied to the host site which may have a convex or concave or a combination of concave and convex surfaces. The adhesive composition may have sufficient cohesion and adhesion to the host site while in its fluid or semi-solid state to resist displacement from gravity, hydrostatic pressure, or fluid flow acting upon it. The structure may be placed into or onto the adhesive composition while in its fluid or semi-solid state in a desired location relative to the surroundings before the adhesive composition hardens, whereupon the structure possesses primary stability. Alternatively, the structure might be placed into or onto the host site in a desired location relative to the surroundings and subsequent to this an adhesive composition might be injected around or through a cannulation or orifice feature of the implant device that which communicates to the surface of the host site before the adhesive composition hardens, whereupon the structure possesses primary stability. Alternatively, the structure might be first coated on some or all of its surfaces with an adhesive composition and subsequently placed onto or into the host site before the fluid adhesive composition hardens, whereupon the structure possesses primary stability.

Figure 4:
FIG. 4 is a schematic drawing of a gap, hole, or void on a surface.
Figure 5:
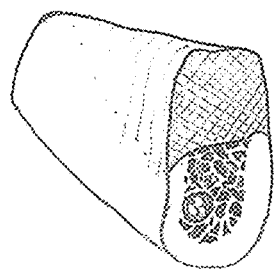
FIG. 5 is a schematic drawing of an adhesive composition used to fill a gap, hole, or void on the surface shown in FIG. 4, according to an embodiment disclosed herein.
Figure 6:
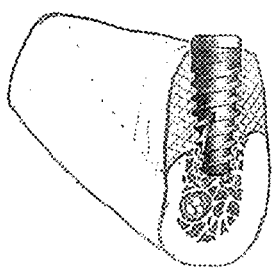
FIG. 6 is a schematic drawing of a structure placed within the gap, hole, or void on the surface shown in FIG. 5 having been filled with an adhesive composition, according to an embodiment disclosed herein.
Figure 7:
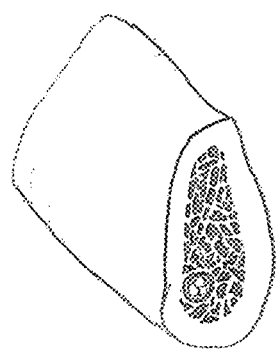
FIG. 7 is an alternate schematic drawing of a gap, hole, or void on a surface.
Figure 8:
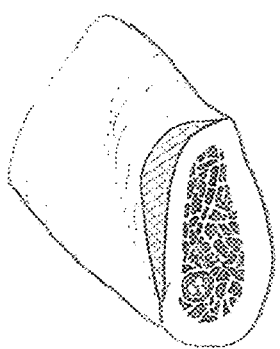
FIG. 8 is a schematic drawing of an adhesive composition used to fill a gap, hole, or void on the surface shown in FIG. 7, according to an embodiment disclosed herein.
Figure 9:
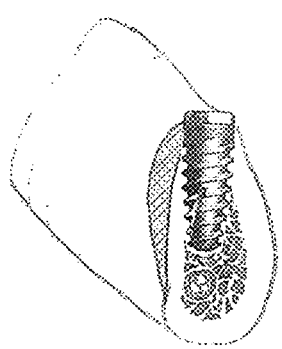
FIG. 9 is a schematic drawing of a structure placed within the gap, hole, or void on the surface shown in FIG. 8 having been filled with an adhesive composition, according to an embodiment disclosed herein.
Figure 10:
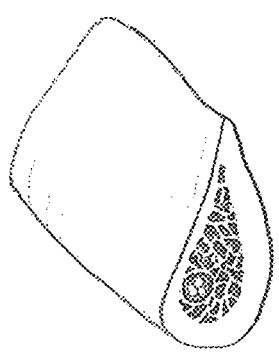
FIG. 10 is an alternate schematic drawing of a gap, hole, or void on a surface.
Figure 11:
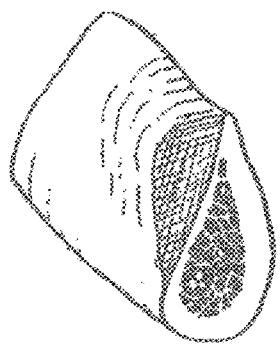
FIG. 11 is a schematic drawing of an adhesive composition used to fill a gap, hole, or void on the surface shown in FIG. 10, according to an embodiment disclosed herein.
Figure 12:
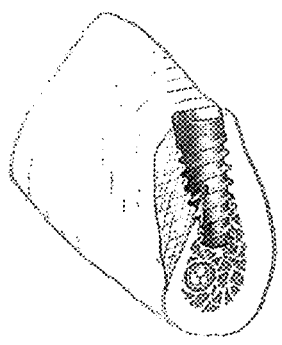
FIG. 12 is a schematic drawing of a structure placed within the gap, hole, or void on the surface shown in FIG. 11 having been filled with an adhesive composition, according to an embodiment disclosed herein.
Figure 13:
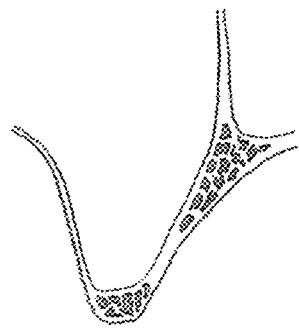
FIG. 13 is an alternate schematic drawing of a gap, hole, or void on a surface.

In other embodiments, the alveolar or residual ridge is augmented with an adhesive composition to create an increase in ridge bone composite volume concurrent with placement of a dental implant per the following technique. As used herein, "alveolar" and "residual" ridge refer to the bony ridge of the maxilla or mandible that contains the alveolar sockets. Generally, the alveolar ridge is referred to as the residual ridge once teeth are lost. As used herein, alveolar ridge and residual ridge may be used interchangeably to refer to the dental ridge. First, the alveolar or residual ridge may require an initial step to prepare the bone surface, which may include drilling or reaming the available bone to a desired state (e.g., as shown in FIGS. 4, 7, and 10). Next, an adhesive composition is adhesively applied to the alveolar or residual ridge (e.g., as shown in FIGS. 5, 8, and 11). A dental implant is placed into the adhesive composition in a desired location relative to the surroundings before the adhesive composition hardens to the solid state, whereupon the implant possesses primary stability. The implant may partially or may not engage bone in the alveolar ridge that was previously prepared (e.g., as shown in FIGS. 6, 9, and 12). Further, the healing, temporary, or definitive abutment, and a temporary or definitive crown may be placed on the dental implant either during the same procedure at a subsequent step or at a subsequent procedure after a sufficient time interval has elapsed for soft tissue and bone healing to occur. The interval might be equal to or less than twenty-four hours, twenty-four hours to one week, one week to two weeks, two weeks to one month, one month to three months, three months to six months, six months to one year, or more than one year. The crown, implant, abutment, material and surrounding bone are all subjected and able to maintain primary stability when subjected to patient loading (e.g., chewing forces).

The adhesion of structures might be performed into the hardened adhesive composition following an interval. The interval might be equal to or less than an hour, more than an hour but less than eight, eight hours to twenty-four, twenty-four hours to one week, one week to two weeks, two weeks to one month, one month to three months, three months to six months, six months to one year, or more than one year. To do so, a preparation may be milled (e.g., drilled) into the substrate composed of the solidified adhesive composition and the underlying or surrounding bone. The structure might be placed directly into the preparation in a desired location relative to the surroundings, whereupon the structure possesses primary stability (e.g., as shown in FIGS. 3, 6, 9, 12, and 15). Alternatively, the preparation might be first partially or totally filled with an adhesive composition and the structure might be subsequently placed into the preparation in a desired location relative to the surroundings while the adhesive composition is in its fluid or semi-solid state and whereby the structure displaces the adhesive composition during placement before the fluid adhesive composition hardens, whereupon the structure possesses primary stability (e.g., as shown in FIGS. 3, 6, 9, 12, and 15). Alternatively, the structure might be placed into the preparation in a desired location relative to the surroundings and subsequent to this an adhesive composition might be injected through a cannulation or orifice feature of the implant device that which communicates to the surface of the preparation before the adhesive composition hardens, whereupon the structure possesses primary stability. Alternatively, the structure might be first coated on some or all of its surfaces with an adhesive composition and subsequently placed into the preparation before the fluid adhesive composition hardens, whereupon the structure possesses primary stability.

In other embodiments, the alveolar or residual ridge is augmented with an adhesive composition to create an increase in ridge volume (width or height) concurrent with placement of a dental implant per the following technique. In some embodiments, the alveolar ridge may require an initial step to prepare the bone surface, which may include drilling or reaming the available bone to a desired state (e.g., as shown in FIGS. 4, 7, and 10). In some embodiments, the adhesive compositions may then be placed or injected into a prepared extraction socket and is allowed to become solid. A preparation can then be milled (e.g., drilled) into the substrate composed of the solidified material and the surrounding bone. Then compositions of either similar or different compositions in their fluid state (i.e., working state) are placed into the preparation and/or applied onto the surface of the implant (e.g., dental implant). The implant is placed into the preparation in a desired location relative to the surroundings before the fluid material hardens to the solidified cement state, whereupon the implant possesses primary stability (e.g., as shown in FIGS. 6, 9, and 12). Further, the healing, temporary, or definitive abutment, and perhaps a temporary or definitive crown may be placed on the dental implant either during the same procedure at a subsequent time interval or at a subsequent procedure after sufficient time has elapsed for soft tissue and bone healing to occur to a desired state. The interval might be equal to or less than twenty-four hours, twenty-four hours to one week, one week to two weeks, two weeks to one month, one month to three months, three months to six months, six months to one year, or more than one year. In some embodiments, the crown, implant, abutment, material and surrounding bone are all subjected and able to maintain primary fixation when subjected to immediate patient loading (e.g., chewing forces). In other embodiments, the crown, implant, abutment, material and surrounding bone are all subjected and able to maintain primary stability when subjected to patient loading (e.g., chewing forces).

In other embodiments, a full thickness incision (e.g., a distant full thickness incision) followed by a tunneling subperiosteal dissection and a subperiosteal placement or injection of the adhesive compositions in contact with bone are used to produce augmentation of the bone volume in the area. This might be a widening of the alveolar ridge where a dental implant placement is desired, but where the width of the residual ridge of bone is marginally insufficient for implant placement. The ridge so augmented is sufficiently broad for an osteotomy to be performed within the original bone volume, either at the time of the original procedure or after a delay of days, weeks, or months, and for the adhesive compositions placed, in the hardened state or as altered by the host, to provide resistance to lateral movement of the rotary cutting instrument during bone preparation and to the implant on placement into its planned relationship to the surrounding host bed.

In other embodiments, with an alveolar residual ridge deficient in width thus limiting implant placement options, a full thickness incision and flap reflection are made, followed by application of an adhesive composition in contact with bone, are used to produce augmentation of the bone volume in the area (e.g., as shown in FIG. 11). This might be a widening of the alveolar ridge where a dental implant placement is desired, but where the width of the residual ridge of bone is initially marginally insufficient for implant placement. The ridge so augmented is as a result then sufficiently broad for an osteotomy to be performed within the original bone volume, either at the time of the original procedure or after a delay of days, weeks, or months, and for the adhesive composition placed, in the hardened state or as altered by the host, to provide resistance to lateral movement of the rotary cutting instrument during bone preparation and to the implant on placement into its planned relationship to the surrounding host bed.

In other embodiments, a full thickness incision (e.g., a distant full thickness incision) followed by a tunneling subperiosteal dissection and a subperiosteal application of an adhesive composition in contact with bone are used to produce augmentation of the bone volume in the area (e.g., as shown in FIGS. 8 and 11). This might be increasing the height of the alveolar ridge where a dental implant placement is desired, but where the height of the residual ridge of bone is initially marginally insufficient for implant placement (e.g., as shown in FIG. 5). The augmented ridge composed of the original bone and the adhesive composition is as a result then sufficiently high for an osteotomy to be performed, either immediately or after a delay of hours, days, weeks, or months, and for the adhesive compositions placed, in the hardened state or as altered by the host, to provide resistance to lateral movement of the rotary cutting instrument during bone preparation and to the implant on placement into its planned relationship to the surrounding host bed.

In other embodiments, with an alveolar residual ridge deficient in height thus limiting implant placement options, a full thickness incision and flap reflection are made, followed by application of an adhesive composition in contact with bone, are used to produce augmentation of the bone volume in the area (e.g., as shown in FIG. 5). This might be to increase the total height of available volume for dental implant placement. The volume so augmented is as a result then sufficiently tall for an implant recipient site to be milled into it, either immediately or after a delay of hours, days, weeks, or months, and for an adhesive compositions placed, in the hardened state or as altered by the host, to provide resistance to lateral movement of the rotary cutting instrument during bone preparation and to the implant on placement into its planned relationship to the surrounding host bed.

In other embodiments, the ridge so augmented is sufficiently broad for an osteotomy to be performed within the volume of the wider solid composed of the bony ridge and the additional adherent material, in the hardened state or as altered by the host. In some embodiments, the implant host bed is a combination of the preexisting bone, the compositions, or the compositions as altered by the host, throughout the length of the implant. In other embodiments, the ridge so augmented is sufficiently high for an osteotomy to be performed within the volume of the higher solid composed of the bony ridge and the additional adherent material, in the hardened state or as altered by the host. Alternatively, the implant placement is delayed until the composition is partially or totally resorbed and replaced by bone. In this embodiment, the most superficial layer of the implant host site bed is the composition or the composition as altered by the host, and the deepest part of the bed is the bone volume present before the composition was placed.

Figure 14:
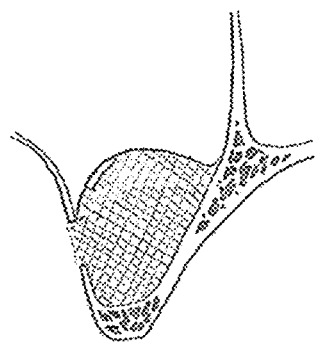
FIG. 14 is a schematic drawing of an adhesive composition used to fill a gap, hole, or void on the surface shown in FIG. 13, according to an embodiment disclosed herein.
Figure 15:
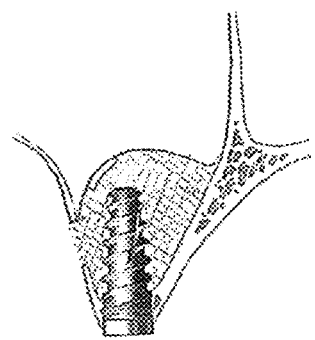
FIG. 15 is a schematic drawing of a structure placed within the gap, hole, or void on the surface shown in FIG. 14 having been filled with an adhesive composition, according to an embodiment disclosed herein.

In some embodiments, a subperiosteal injection or placement of the adhesive compositions in contact with bone is performed between the mucoperiosteum of a facial sinus or another air space (e.g., the nasal airway, e.g., as shown in FIG. 14). In some embodiments, the facial sinus comprises the paranasal sinus, e.g., the maxillary sinus. This might be an augmentation in height of the bone volume where a dental implant placement is desired, but where the height of the residual bone between the oral cavity and the sinus air space is insufficient for implant placement. The bone so augmented is sufficiently high for an osteotomy to be performed within the volume of the higher solid comprised of the bone and the additional adherent material, in the hardened state or as altered by the host. Alternatively, the implant placement is delayed until the composition is resorbed and replaced by bone, in part or totally. In this embodiment, the deepest layer of the implant host site bed is the composition or the composition as altered by the host, and the most superficial part of the bed is the bone volume present before the material was placed.

In some embodiments, the compositions might be adhesively applied to bony walls of a gap or a discontinuity between bone surfaces which are indicated for closure because the gap or the discontinuity of bone causes a disability, a dysfunction, or is otherwise undesirable. In some embodiments, the gap or the discontinuity of bone is undesirable because of loss of load-bearing function. These may include a gap or discontinuity which is congenital (e.g., cleft palate), a result of trauma (e.g., bone fracture), result of inappropriate healing (e.g., fibrous union), a result of a resection of bone (e.g., neoplasm, necrosis, or infection), or a result of procedure involving cutting or segmentation of bone in order to change its size, shape, or contour (e.g., orthognathic procedure, or correction of deformed long bones resulting from congenital, metabolic or dietary problems). The composition might be used in conjunction with fixation devices, such as microplates, bone pins and screws, or with shape and volume preserving devices, such as titanium meshes or cages, which relate the bone fragments across the gap or exclude other tissues, or it may be used alone or in combination of several formulations of the composition including those that release substances intended to affect surrounding tissues and environment. In this embodiment, the composition performs a bridging function with respect to existing elements of the skeleton, providing continuity of contour, a mechanical connection, and preventing other tissues from proliferating while bone tissue replaces the solidified material. In some embodiments, the mechanical connection is a load-bearing connection.

In some embodiments, the disclosure features a method of reinforcing a bone (e.g., osteoporotic, osteopetrotic, or affected by osteogenesis imperfecta) at risk of fracture, the method comprising: a) preparation of an adhesive composition comprising a multivalent metal salt and a small organic phosphate compound in an aqueous solution or suspension; b) adhesive application of the composition to the desired region of the bone and also adhesively applied to one, or plurality of rigid, or semi-rigid devices (e.g., plates, rods, strips, fibers, or bands) comprised of metal or other biocompatible material; c) applying the device of b) adhesively attached to the bone to the desired region of bone; and d) allowing the composition to remain undisturbed until the composition is hardened, cured, or resorbed and replaced by bone. In some embodiments, the bone is osteoporotic, osteopenic, osteopetrotic, or affected by osteogenesis imperfecta.

In some embodiments, the disclosure features a method of repairing a fractured bone (e.g., osteoporotic femur) fracture, the method comprising: a) preparation of an adhesive composition comprising a multivalent metal salt and a small organic phosphate compound in an aqueous solution or suspension; b) adhesive application of the composition to the desired region of the bone and also adhesively applied to one, or plurality of rigid, or semi-rigid devices (e.g., plates, rods) comprised of metal or other biocompatible material; c) applying the device of b) adhesively attached to the bone to the desired region of bone; and d) allowing the composition to remain undisturbed until the composition is hardened, cured, or resorbed and replaced by bone.

Figure 18:
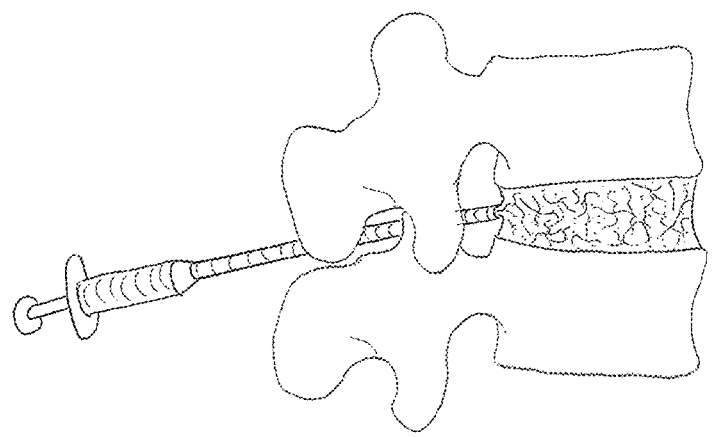
FIG. 18 is an alternate schematic drawing of an adhesive composition being delivered to an application site via injection, according to an embodiment disclosed herein.
Figure 21:
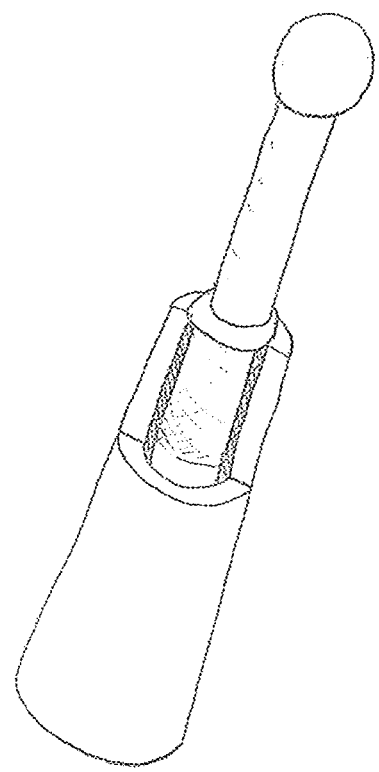
FIG. 21 is a schematic drawing of an adhesive composition used to create a seal, for example by filling a gap, hole, or void, in a structure application site, according to an embodiment disclosed herein.
Figure 22:
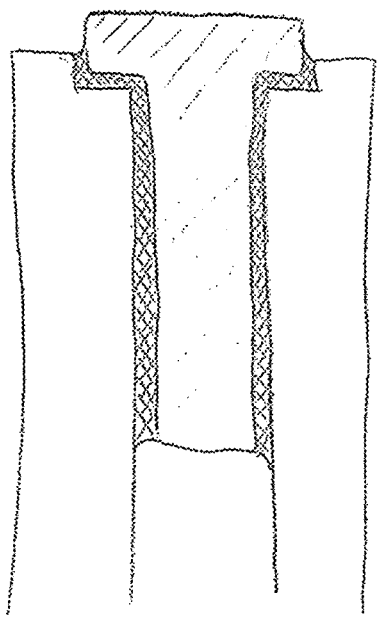
FIG. 22 is an alternate schematic drawing of an adhesive composition used to create a seal, for example by filling a gap, hole, or void, in a structure application site, according to an embodiment disclosed herein.

In some embodiments, the composition is adhesively applied to a gap, discontinuity, or loss of volume in bone (e.g., femur, e.g., as shown in FIGS. 21-22; alveolar ridge, e.g., as shown in FIGS. 4, 7, 10, and 13), or to a gap, discontinuity, or loss of volume between bones (e.g., spinal processes, vertebral bodies as shown in FIGS. 17 and 18). In some embodiments, the gap or the discontinuity causes a disability, a dysfunction, or is otherwise undesirable. The gap or discontinuity may be congenital (e.g., cleft palate), a result of trauma (e.g., bone fracture), a result of a resection of bone (e.g., neoplasm, necrosis, or infection), or a result of procedure involving cutting or segmentation of bone in order to change its size, shape, or contour (e.g., orthognathic procedure, correction of deformed long bones resulting from congenital, metabolic or dietary problems). In other embodiments, the gap or discontinuity may be a result of a resection of soft tissue (e.g., removal of cartilage or discectomy, e.g., as shown in FIGS. 17 and 18). In some embodiments, the composition is used alone. In other embodiments, the composition is used in conjunction with rigid devices, such as microplates, plates and objects of other shapes, composed of metal or other solid material, shape and volume preserving devices, such as titanium meshes, which relate the bone fragments across the gap or exclude other tissues, or it may be used alone or in combination of several formulations of the composition including those that release substances intended to affect surrounding tissues and environment. In some embodiments, the composition may be used in conjunction with interbody devices (e.g., cages, e.g., as shown in FIG. 17). In this embodiment, the composition performs a bridging function with respect to existing elements of the skeleton, providing continuity of contour, a mechanical connection, and preventing other tissues from proliferating while bone tissue replaces the solidified material.

Figure 16:
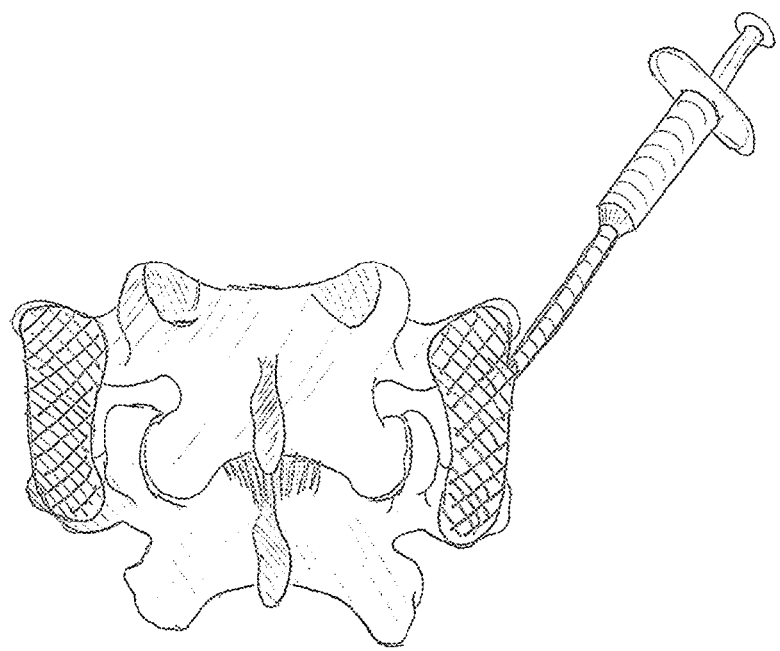
FIG. 16 is a schematic drawing of an adhesive composition being delivered to an application site via injection, according to an embodiment disclosed herein.
Figure 19:
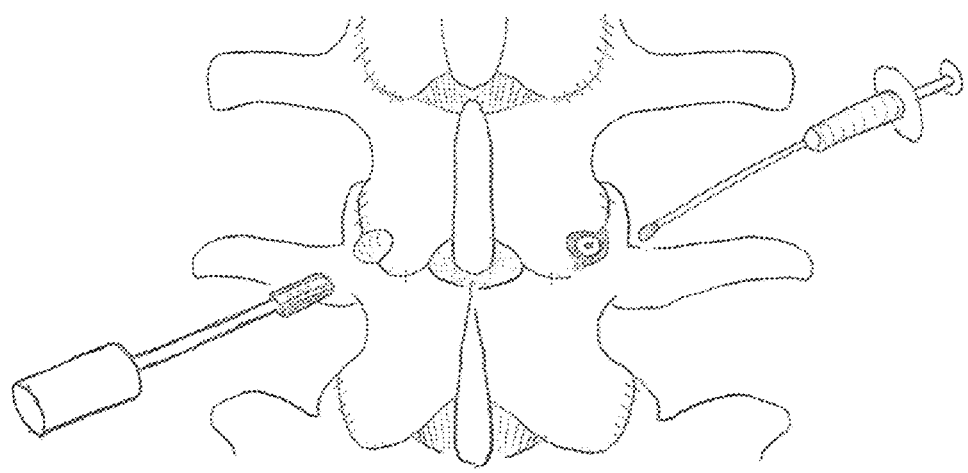
FIG. 19 is an alternate schematic drawing of an adhesive composition being delivered to an application site via injection, according to an embodiment disclosed herein.
Figure 20:
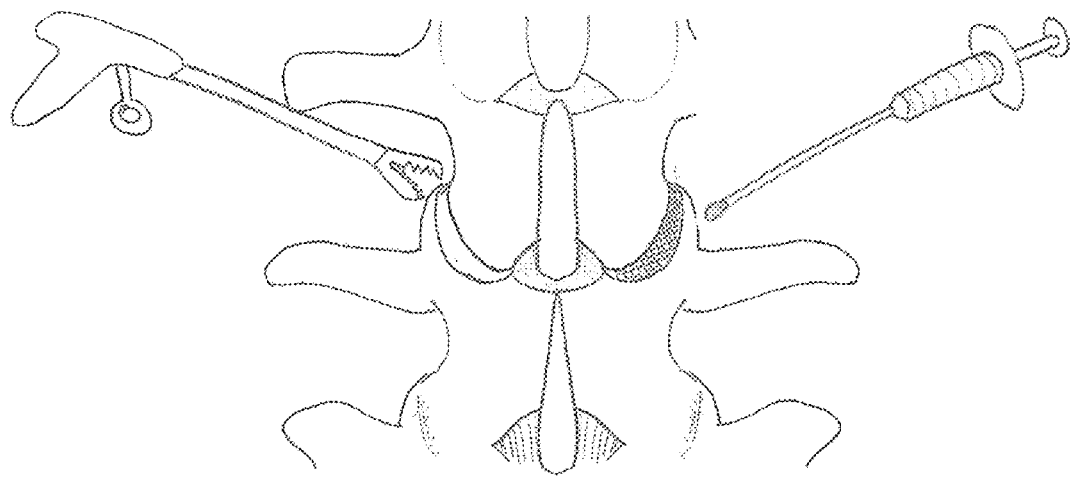
FIG. 20 is an alternate schematic drawing of an adhesive composition being delivered to an application site via injection, according to an embodiment disclosed herein.

In some embodiments, the adhesive composition is applied between articulating bone surfaces (e.g., facet joints, e.g., as shown in FIG. 19) or is applied to adjacent bone surfaces to bridge a gap space (e.g., between vertebral bodies. e.g., as shown in FIG. 18; between transverse processes, e.g., as shown in FIG. 16; or between spinous processes) to prevent relative displacement of the bone surfaces (e.g. spinal fusion procedures) and to provide load bearing support with or without supportive implants devices (e.g., screws, plates, interbody cages, e.g., as shown in FIG. 17). These applications might be made singly or to provide multipoint fixation when applied in several of the above or other, loci.

In some embodiments, the adhesive compositions are adhesively placed or injected in contact with bone, into a space adjacent to or a gap between volumes of bone, where it is desired to affix implants or other devices (e.g., as shown in FIGS. 21-22). The device might be placed, embedded, or otherwise affixed to the composition and the host bed at a time prior to the composition adopting the cement state, during the setting process, after the composition is solid, or after the composition is partially or totally replaced with bone tissue.

In some embodiments, the adhesive compositions are placed or injected into a bone defect associated with a root of a tooth (e.g., a periodontal defect, a periapical defect) and allowed to solidify. In some embodiments, the bone defect associated with a root of a tooth is a periodontal or periapical defect. The compositions may then be replaced by bone providing increased mechanical stability to the tooth and also barring environmental microbiota from access to the root surface and the interior of the alveolar socket.

In other embodiments, the adhesive compositions are placed or injected into a bone defect associated with a dental implant (e.g., a periimplantitis defect) and allowed to solidify. The compositions may then be replaced by bone providing increased mechanical stability to the implant and also barring environmental microbiota from access to the implant surface and the surrounding bone.

In some embodiments, the adhesive compositions might have adhesive properties toward soft tissues. A layer of the composition might be applied as an adhesive to immobilize soft tissue flaps, fragments, or zones. The attachment of the composition to the soft tissues might be durable enough and strong enough to close wounds. The attachment of the composition might provide a barrier to flow of fluids from one side of the attachment to another side. The attachment of the composition might provide a barrier to movement of microbes from one side of the attachment to another side. The surface of the composition might be a barrier to the movement of soft tissue cells (e.g., fibroblasts) into the interior of the set material. The surface of the composition might be a barrier to the movements of microbes into the interior of the set composition.

In some embodiments, the adhesive compositions might be injected or otherwise placed at the percutaneous or permucosal site of an implant or device placement to seal the site from incursion of fluids, materials, and microbiota or their products deeper into the wound. This application might be contemporaneous with the initial placement of the implant or another later procedure involving the implant. The implant might be a dental implant, a maxillofacial prosthesis fixation implant or any other implant with a permucosal or percutaneous component. In some embodiments, the implant may be a prosthetic limb element.

In other embodiments, the adhesive compositions might be injected, layered, sprayed, brushed, or otherwise applied in one or more variants of composition to a surgical wound in areas where the bony tissue is present near the gingiva, mucosa, skin, or other element of the integument, thereby fixating the soft tissue margins and blocking movement of liquids, materials, and microbiota and their products deeper into the wound.

In other embodiments, the adhesive compositions may be used to reconstruct and adjoin a fissure or gap that has resulted from a congenital deformity, such as, but not limited to a cleft lip and palate. The compositions could be utilized to restore the bone deformity to a primary palate by using the compositions to fill and adhere the maxillary and medial nasal processes.

In other embodiments, the adhesive compositions may be used in the field of plastic surgery as an onlay graft, which can be applied and adheres to the outer surfaces of bone in the facial region. The composition may be adhesively applied as a fluid or putty like substance, and contoured or molded to a desired cosmetic profile or contour before it hardens. The composition may be resorbed and replaced by bone over time, while maintaining the original volume and shape formed during application. The composition could be applied, but not limited, to the chin, cheek, mid-face, or forehead regions.

In some embodiments, the adhesive compositions may be adhesively applied to affix the bone fragment removed to create a window to allow access for grafting in a sinus lift procedure or a Caldwell-Luc procedure. The adhesive composition may be injected, sprayed, brushed or otherwise applied in one or more compositional variants to fill the gap and/or affix the bony fragment or flap created by surgical instruments to allow access to the sinus cavity.

In some embodiments, the compositions may be adhesively applied to affix the bone fragment or fragments removed to create access for procedures within spaces enclosed by bone (e.g., intracranial space for brain surgery procedures). In some embodiments, creating access within spaces enclosed by bone comprises providing cranial flap access to the intracranial space, e.g., for brain surgery procedures. The adhesive composition may be injected, sprayed, brushed or otherwise applied, in one or more compositional variants, to affix the bony fragment, bone fragments, or bone flap to the anatomical site from which it was removed in the course of gaining the said access by surgical instruments.

In some embodiments, the adhesive compositions may be applied to obturate an opening in bone or a communication between spaces or potential spaces separated by the said bone. This opening might be a congenitally, pathologically, traumatically or surgically generated bony fenestration, dehiscence, or communication (e.g., oral-antral fistula, Caldwell-Luc procedure access opening, sinus elevation graft access opening) or any other. The adhesive composition may be injected, sprayed, brushed or otherwise applied in one or more compositional variants, in conjunction or without other materials possibly serving as carrier or matrix, to occlude the passage from one to another side of the bone through gap, fistula, or communication channel.

In some embodiments, the adhesive composition might serve as a seal to close off the communication between an intracranial or spinal space bathed in the cerebrospinal fluid and the exterior of the body: the method comprising: preparation of an adhesive composition comprising a multivalent metal salt and a compound of a Formula (e.g., Formula (I), Formula (II), Formula (III), Formula (IV), or combinations thereof), in an aqueous medium; application of the adhesive composition into or onto said communication, e.g., crevice, fistula, or tear; and allowing the composition to remain undisturbed until the composition is hardened, cured, or resorbed and replaced by bone.

In some embodiments, the disclosure features a method of adhesively repairing a defect in a tooth, the method comprising: a) preparation of an adhesive composition comprising a multivalent metal salt and a compound of a Formula (e.g., Formula (I), Formula (II), Formula (III), Formula (IV), or combinations thereof), in an aqueous medium; application of the composition into or onto said tooth defect; and allowing the composition to remain undisturbed until the composition is hardened, cured, or resorbed and replaced by bone.

In some embodiments, the adhesive compositions may be adhesively applied to the surface of a tooth. The adhesive composition may be injected, sprayed, brushed or otherwise applied in one or more compositional variants to fill the gap in tooth substance resulting from the removal of dental caries or to a surface exposed by tooth fracture or abrasion, attrition, abfraction, or erosion of the tooth substance.

In some embodiments, the adhesive compositions may be adhesively applied to the surface of a tooth or dental restorative material to lute or adhesively fixate them. The adhesive composition may be injected, sprayed, brushed or otherwise applied in one or more compositional variants to fill the gap in tooth substance resulting from the removal of dental caries or to a surface exposed by tooth fracture or abrasion, attrition, abfraction, or erosion of the tooth substance.

In other embodiments, the adhesive compositions are used to treat or heal a subject suffering from a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, severe and handicapping malocclusion, osteonecrosis, or other genetic or developmental disease. In some embodiments, the adhesive compositions are used to repair a defect in a bone caused by a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, or other genetic or developmental disease. In some embodiments, the adhesive compositions are used to strengthen a bone in a subject that has been weakened by a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, or other genetic or developmental disease. In some embodiments, the subject has experienced a trauma, such as a broken bone, fractured bone, or damaged tooth. In some embodiments, the subject has experienced tooth decay. In some embodiments, the subject is undergoing a plastic surgery procedure. The compositions and methods may be used to treat a subject suffering from or afflicted with any disease or condition that impacts the structural integrity of the bony skeleton. In some embodiments, the subject is a child. In some embodiments, the subject is an adult. In some embodiments, the subject is a non-human animal.

Industrial Uses of the Adhesive Compositions

The adhesive compositions may be useful in a wide variety of applications, for example, non-medical applications, including industrial applications. In some embodiments, the adhesive compositions may be used to adhere a structure to a surface. In some embodiments, the adhesion of said structure is temporary, such that said structure is removed after a period of time (e.g., greater than about 1 hour, about 2 hours, about 12 hours, about 24 hours, about 1 week, about 1 month, about 6 months, about 1 year, about 5 years). In other embodiments, the adhesion of said structure is permanent or intended to be permanent or until the material is resorbed and replaced with another material.

In other embodiments, the adhesive compositions may be used to fill a gap, hole, or void in a surface either before or after placement of a structure into or onto a surface. It is envisioned that this particular application may be useful when the core diameter of the gap, hole, or void is larger than the size of the structure. In this instance, the adhesive composition may impart additional strength, fixation, stability, durability, or other advantageous property to the attached structure at the attachment site. In other embodiments, the adhesive composition may impart fixative strength to the attached structure at the attachment site. In some embodiments, the adhesive compositions may support new material at the attachment site. In additional embodiments, the adhesive compositions may be used to fill gaps created in or at the attachment site to create a seal, prevent leakage, or prevent microbial growth.

Adhesive compositions disclosed herein may be applied, for example, to seal or repair a crack, fissure, leak, or defect in an object, reinforce the strength of a damaged structure, join separated objects, fill space to connect and immobilize structures (e.g., screws, trusses) or seal or secure objects that would otherwise separate due to vibration, cyclic straining, or buoyancy forces (e.g. wave action, wake, wind or current flutter, floods), rain, hail, snow, sleet, or wind.

In one embodiment, the adhesive composition may be applied along a surface-spanning defect in an object and may be used as a patch. In one embodiment, the adhesive composition may be applied along a surface-spanning crack between two objects in an object and may be used, for example, as a tape. In one embodiment, the adhesive composition may be applied as an interposition device between two objects and may be used, for example, as a patch or plug. In one embodiment, the adhesive composition may be applied to the exterior or interior of the surface of a defect in or on an object and may be used, for example, as a patch or plug.

In certain embodiments, the surface to which the adhesive composition is applied comprises a metal, e.g., silicon, aluminum, titanium, cobalt, chromium, tantalum, molybdenum, copper, silver, gold, zinc, or iron. The surface to which the adhesive device is applied may be a metallic coating (e.g., nickel plated, chrome placed, galvanized, etc. objects) The surface to which the adhesive device is applied may be a metallic alloy (e.g., bronze, brass, stainless steel, titanium-aluminum, titanium-aluminum-vanadium, cobalt-chromium, nickel-chrome, etc.), or may include an industrial material surface used in a marine, plumbing, earth-based (e.g., basalt, granite, limestone, sandstone, slate, etc.), paving (e.g., asphalt, concrete, cement), or piping setting. In certain embodiments, the surface to which the adhesive composition is applied comprises a glass surface (e.g., glass (e.g., silica, aluminosilicate, borosilicate) or glazed objects).

In some embodiments, the surface to which the adhesive composition is applied may require or be related to a permanent application. In other embodiments, the surface to which the device is applied may require or be related to a rapid or temporary application, for example, in the case of a leaking pipe or a leaking or sinking marine vessel (e.g., a boat). In some embodiments, the surface to which the adhesive composition is applied may require or be related to holding down and securing an object (e.g., tent, canopy, plant, tree, barrier, fence, net, dam, signage, appliance, boat, car, mobile home or camper) to the ground, pavement, or to any other device anchored to the ground that would otherwise separate and be mobile due to vibration, cyclic straining, or buoyancy forces (e.g. wave action, wake, wind or current flutter, floods), rain, hail, snow, sleet, or wind. Compositions disclosed herein may be applied to any such surface.

Methods of Use of the Composition

Adhesive compositions disclosed herein may be used in a variety of applications, for example, medical, non-medical, and industrial applications. Methods of use may comprise applying the adhesive composition to a site in need of repair or adhesion. Methods of use may comprise applying pressure to one or more surfaces or objections for a predetermined period of time, for example, to hold a surface or object in place until the composition hardens.

In some embodiments, the method of use further comprises observation of a defect in an object (e.g., a wet, submerged, immersed, leaking, weeping, or oozing object) from which a fluid (e.g., an aqueous fluid) is emanating through a crack, fissure, breach or defect in the surface and a determination of the specific type of device (e.g., an adhesive device described herein) or the specific components thereof to utilize to seal or repair said object. The adhesive composition of the present disclosure may be applied to an object in a number of ways. For example, in some embodiments, the method of application comprises placement on an object that is wet, submerged, immersed, leaking, weeping, or oozing from the surface. Exemplary crack, fissures, breaches or defects in a surface include, but are not limited to, perforations, ruptures, pores, pits, tears, corrosions, erosions, abrasions, fractures, and the like.

In certain embodiments, the method of use comprises application of the adhesive composition to a perforated object from which a flow of an aqueous medium (e.g., an aqueous medium described herein) emanates from the perforation. In such cases, the flow of the aqueous fluid may interact with the adhesive composition or components thereof, allowing the composition to solidify while in contact with the surface. In some embodiments, the method comprises observation of said interaction between the adhesive composition and the aqueous medium. In other embodiments, the method comprises application of the adhesive composition to a wet surface, wherein the device and the aqueous medium (e.g., an aqueous medium described herein) interact, for example, resulting in the solidification and bonding of the adhesive composition to the surface. In still other embodiments, the method comprises wetting the adhesive composition with an aqueous medium, followed by application of the adhesive composition to a surface, resulting in the solidification and bonding of the adhesive composition to the surface. Exemplary perforated objects include, but are not limited to, pavement, bone, pipe, boat hull, pane of glass, boat deck, storage vessel, tank, or industrial process equipment. The perforated object may comprise metal or have a metal surface, wherein the metal surface is coated with chromium, nickel, zinc, tin, silver, or copper. These exemplary metal surfaces may also be coated through natural oxidation or corrosion processes to be titanium oxide, aluminum oxide, zinc oxide, chromium oxide, nickel oxide, tin oxide, silver oxide, iron oxide, or copper oxide. In any and all of these embodiments, the method may further comprise observation of said interaction between the adhesive composition and the aqueous medium.

In other embodiments, the method comprises use of the adhesive composition as a splint through application of the device to the outer surface of an object or inner surface through a central shaft or canal of an object (e.g., separated pipe or pipe segments, or to reattach broken coral or transplanted coral to a stable substrate (e.g., native coral reef or artificial coral reef substance)). In certain embodiments, the adhesive composition is applied to one aspect of a separated object or multiple aspects of the separated object. The device may be used as a splint by covering the area of the separated object in between or near the fracture line (e.g., in case of pipes, beams, or stems of coral).

In other embodiments, the method comprises use of the adhesive composition as an interposition between surfaces to be joined, e.g., by injecting the adhesive composition within the separation line, or between the separated pieces of an object, or within the separation space between the objects (e.g., broken or cracked beams, trusses, pipes, hulls, decks, bolts, screws, rods, pins, nuts). Upon exposure to an aqueous medium (e.g., an aqueous medium described herein), the adhesive composition may solidify, adhere to, or seal the adjoining surfaces. The solidified adhesive composition has structural strength to reinforce the damaged joint enabling load bearing properties. An exemplary use of the adhesive composition at the interposition between two surfaces is the reattachment of broken coral or transplanted coral to a stable substrate (e.g., native coral reef or artificial coral reef substance).

In other embodiments, the method comprises use of the adhesive composition to stabilize mechanical relationships between elements in industrial settings (e.g., nuts and bolts, pipes and fittings, compression plates, bulkhead fittings, etc.) of structures subjected to vibration, cyclical straining or other dislodging conditions.

In other embodiments, the method further comprises use of an additional access device to aid in the application of the adhesive composition to a surface or region which is difficult to reach or to which minimally invasive approaches are desired. Exemplary additional access devices to aid in such application include, but are not limited to, an access tube, cannula, guide, or pipe. In some embodiments, the adhesive composition is injected or pushed through the additional access device.

Kits

In some embodiments, different variants of the components of the adhesive composition may be packaged and marketed as a kit for specific applications.

In some embodiments, the kits may comprise an adhesive composition comprising a multivalent metal salt (e.g., tetra-calcium phosphate) with a compound of a Formula (e.g., Formula (I), Formula (II), Formula (III), Formula (IV), or combinations thereof), and an aqueous medium present together and sealed under good packaging practices to preserve the shelf life of the individual components. The adhesive composition may be present in a container. In some embodiments, preservation of the shelf life of the components within the kit includes a barrier to moisture ingress or maintenance of sterility. If additives are included in said kit, they may be packaged within this container or within a separate container or compartment (e.g., multi-barrel syringe or multi-chambered cartridge or capsule). The aqueous medium (e.g., water, solution, or suspension), if included, may be provided in a separate container or compartment. The kit may include additional components, for example devices, for the preparation or application of the adhesive compositions, such as mixing bowls or surfaces, stirring sticks, spatulas, syringes, heat guns, agitators, triturators, applicator hand pieces, pumps, or other preparation or delivery devices. The kit may include instructions for use, for example, instructions for a method of using an adhesive composition, as disclosed herein.

EXAMPLES

Example 1

Exemplary Compounds

Listed on Table 1 are exemplary compounds that were found to produce self-setting adhesive compositions.

Exemplary adhesive compositions were prepared by providing the compounds listed in Table 1 and tetra-calcium phosphate in a suitable receptacle and mixing with water to achieve the desired consistency. While water was used as the aqueous medium in the present compositions, the aqueous medium may instead be blood, saliva, serum, or a blood-based solution or suspension. In the present compositions, the solid components (compounds, tetra-calcium phosphate) were provided as particles. However, the solid components listed in the table may be provided in particle, granule, or fiber form, and the size of each of the components may vary as described in the Detailed Description. In some embodiments, the resulting properties, such as working and setting time, may be affected by these changes. The specific mean particle, granule, or fiber size for each solid component was selected to satisfy the use requirements as described in each of the embodiments.

Exemplary adhesive compositions were prepared comprising the compounds shown in Table 1 as described in Table 2. The compounds comprising glyphosine, O-Phospho-L-serine (OPLS), ethylenediaminetetraacetic acid (EDTA), propylenediamine tetraacetic acid, and aminotris (methylenephosphonic acid) (ATMP) were injectable, adhesive, tacky, and self-setting. The quantities of each of the components listed may be altered or adjusted in relation to the other components in the composition, for example, to alter or adjust at least one physical property of the composition. After mixing, the compositions described were applied to the desired site and the adhesive properties examined, e.g., for tensile strength and durability.

TABLE 1

Exemplary Compounds

| Formula | Compound Name | Structure |
|---|---|---|
| I-a | N,N-Bis(phosphonomethyl)glycine (Glyphosine) | 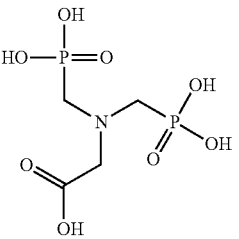 [SMILES: O=C(O)CN(CP(=O)(O)O)CP(=O)(O)O] |

TABLE 1-continued

| Exemplary Compounds | | |
|---|---|---|
| Formula | Compound Name | Structure |
| I-b | (Nitrilotris(methylene))triphosphonic acid (ATMP) | |
| II-a | Ethylenediamine tetraacetic acid (EDTA) | |
| II-b | Egtazic acid (EGTA) | |
| II-c | Propylenediaminetetraacetic acid (PDTA) | |
| III-a | Malonic Acid | |
| III-b | Citric Acid | |

TABLE 1-continued

Exemplary Compounds

| Formula | Compound Name | Structure |
|---|---|---|
| IV-a | O-Phospho-L-Serine (OPLS) | 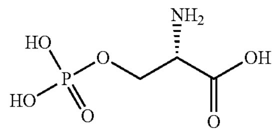 |

TABLE 2

Exemplary Adhesive Compositions

| Composition | Compound Name | Compound Formula | Compound (mg) | Tetracalcium Phosphate (mg) | Water (μl) |
|---|---|---|---|---|---|
| 1A | Glyphosine | I-a | 711 | 800 | 540 |
| 1B | ATMP | I-b | 202 | 800 | 270 |
| 1C | EDTA[1] | II-a | 395 | 800 | 270 |
| 1D | EDTA[2] | II-a | 790 | 800 | 370 |
| 1E | EDTA[3] | II-a | 550 | 800 | 320 |
| 1F | PDTA | II-a | 414 | 800 | 270 |
| 1G | Malonic Acid | III-a | 281 | 800 | 135 |
| 1H | Citric Acid | III-c | 519 | 800 | 260 |
| 1I | OPLS | IV-a | 500 | 800 | 270 |

Example 2

Adhesive Shear Strength to Bone Substrate Surfaces

The shear strength was measured to rupture the bond formed between two bone substrate surfaces that were adhered together using many of the exemplary adhesive compositions listed in Table 2. The bone substrate was from bovine origin and was prepared as a rectangular block with dimensions of 8.5 mm width×8.5 mm height×20 mm length and the surfaces were polished. For each test, two blocks of bone were adhered together. Prior to testing, the end faces of the two bone blocks (8.5 mm×8.5 mm) were dampened with phosphate buffered saline (PBS) solution. Each composition was prepared by mixing for 20 seconds after addition of the water to ensure a smooth consistency in a 25 mL capacity silicone mixing bowl using a stainless steel spatula. After mixing, the composition was loaded into a 3 cc capacity slip tip syringe and immediately injected onto the end face of each bone block. Immediately thereafter, the bone block end faces covered with adhesive composition were apposed to each other, aligned and compressed. The excess adhesive composition that squeezed out from the joint was removed with a spatula. The adjoined blocks were placed into a fixture that applied a slight compressive force (3 to 5 N) for 4 minutes from the start of mixing, corresponding to the working period of the compositions. Thereafter, the blocks were removed from the fixture and submerged into a phosphate buffered saline (PBS) solution bath at 37° C. to allow the compositions to cure for 24 hours from the start of mixing. The adhered set of cubes were tested at either t=10 minutes, t=1 hour, or t=24 hours from the start of mixing. After the 24 hour curing time, the blocks were removed from the PBS bath for shear testing. The proximal block of the adhered block set was secured in a stable fashion to prevent movement within a sample holding fixture up to within 1.0 mm of the adhered joint mounted to an Instron® (Norwood, MA) 5969 axial load frame. The distal block of the adhered block set was cantilevered from the sample holding fixture. The Instron® crosshead with an attached anvil fixture was lowered until the distal surface of the anvil was within 0.5 mm of the top surface of the distal bone block and within 1.0 mm of adhered joint. The test was run with the crosshead speed at 2 mm/minute. Table 3 shows the results for the average shear stress (MPa) and standard deviation (MPa) after 24 hours of cure in order to rupture the bond formed at the joint between the adhered bone blocks.

TABLE 3

Adhesive Shear Strength to Rupture Bond of Bone Blocks Adhered Together after Exemplary Adhesive Compositions Cured for 24 Hours in PBS Solution

| Composition | Compound name | Average Shear Stress (MPa), n = 3 | Standard Deviation (MPa) |
|---|---|---|---|
| 1A | Glyphosine | 0.37 | 0.09 |
| 1B | ATMP | 0.35 | 0.18 |
| 1C | EDTA[1] | 1.76 | 0.58 |
| 1D | EDTA[2] | 1.30 | 0.73 |
| 1E | EDTA[3] | 2.23 | 0.79 |
| 1F | Propylenediaminetetraacetic Acid | 0.18 | 0.02 |
| 1G | Malonic Acid | 1.68 | 0.54 |
| 1H | Citric Acid | 3.16* | n/a |
| 1I | OPLS | 2.36 | 0.23 |

*n = 2 samples tested

Example 3

Adhesive Shear Strength to Various Substrate Surfaces

The shear strength was measured to rupture the bond formed between various substrate surfaces (e.g., titanium, glass, aluminum, steel, stainless steel, cement, brick, zirconia) that were adhered together using many of the exemplary adhesive compositions listed in Table 2. Each substrate was prepared as a rectangular block with dimensions of 8.5 mm width×8.5 mm height×20 mm length and the surfaces were polished. For each test, two blocks for a given substrate were adhered together. Prior to testing, the end faces of the two substrate blocks (8.5 mm×8.5 mm) were dampened with phosphate buffered saline (PBS) solution. Each composition was prepared by mixing for 20 seconds after addition of the water to ensure a smooth consistency in a 25 mL capacity silicone mixing bowl using a stainless steel spatula. After mixing, the composition was loaded into a 3 cc capacity slip tip syringe and immediately injected onto the end face of each block. Immediately thereafter, the block end faces covered with adhesive composition were apposed to each other, aligned and compressed. The excess adhesive composition that squeezed out from the joint was removed with a spatula. The adjoined blocks were placed into a fixture that applied a slight compressive force (3 to 5 N) for 4 minutes from the start of mixing, corresponding to the working period of the compositions. Thereafter, the blocks were removed from the fixture and submerged into a phosphate buffered saline (PBS) solution bath at 37° C. to allow the compositions to cure for either 1 hour, 24 hours, or 72 hours from the start of mixing. After curing, the adhered block set was removed from the PBS bath for shear testing. The block set was secured in a stable fashion to prevent movement within a sample holding fixture mounted to an Instron® 5969 axial load frame. The Instron® was run with the crosshead speed at 2 mm/minute. Table 4, Table 5, and Table 6 show the results for the shear stress (MPa) after 1 hour of cure, 24 hours of cure, and 72 hours of cure, respectively, in order to rupture the bond formed at the joint between the various substrate blocks using the various exemplary adhesive compositions.

TABLE 4

Adhesive Shear Strength to Rupture Bond of Various Substrate Blocks Adhered Together after Exemplary Adhesive Compositions Cured for 1 Hour in PBS Solution

| | | Shear Stress (MPa) at Bond Failure after 1 Hour Cure in PBS Solution | | | | | | | |
|---|---|---|---|---|---|---|---|---|---|
| Composition | Compound name | Titanium | Glass | Aluminum | Steel | Stainless Steel | Cement | Brick | Zirconia |
| 1E | EDTA | 3.48 | 0.89 | 1.25 | nt | 1.85 | 0.81 | 1.20 | nt |
| 1G | Malonic Acid | nt | 0.70 | nt | nt | nt | 1.69 | nt | nt |
| 1I | OPLS | 3.48 | 3.33 | 2.80 | 2.88 | 5.49 | 4.11 | 2.34 | 3.86 | nt = not tested

TABLE 5

Adhesive Shear Strength to Rupture Bond of Various Substrate Blocks Adhered Together after Adhesive Compositions Cured for 24 Hours in PBS Solution

| | | Shear Stress (MPa) at Bond Failure after 24 Hour Cure in PBS Solution | | | | | | | |
|---|---|---|---|---|---|---|---|---|---|
| Composition | Compound name | Titanium | Glass | Aluminum | Steel | Stainless Steel | Cement | Brick | Zirconia |
| 1A | Glyphosphine | 1.46 | nt | nt | nt | 0.99 | 0.72 | nt | nt |
| 1E | EDTA | 4.27 | nt | 1.31 | 2.93 | nt | 1.97 | nt | nt |
| 1G | Malonic Acid | 1.62 | nt | nt | nt | nt | 1.61 | nt | nt |
| 1H | Citric Acid | 4.27 | nt | nt | nt | nt | nt | nt | nt |
| 1I | OPLS | nt | 3.94 | 3.72 | 1.57 | 6.37 | 2.50 | 2.93 | 3.12 | nt = not tested

TABLE 6

Adhesive Shear Strength to Rupture Bond of Various Substrate Blocks Adhered Together after Adhesive Compositions Cured for 72 Hours in PBS Solution

| | | Shear Stress (MPa) at Bond Failure after 72 Hour Cure in PBS Solution | | | | | | | |
|---|---|---|---|---|---|---|---|---|---|
| Composition | Compound name | Titanium | Glass | Aluminum | Steel | Stainless Steel | Cement | Brick | Zirconia |
| 1A | Glyphosphine | 2.24 | nt | nt | nt | 1.72 | 0.52 | nt | nt |
| 1E | EDTA | 2.13 | nt | 0.75 | nt | 0.90 | 2.31 | 1.34 | nt |
| 1G | Malonic Acid | 2.65 | 0.75 | nt | nt | 0.70 | 3.14 | nt | nt |
| 1I | OPLS | 6.55 | 2.90 | 2.98 | 1.35 | 4.37 | 2.74 | 3.41 | 3.54 | nt = not tested

Example 4

Tack Tensile Strength to Titanium Substrate Surfaces Adhered Together

Testing was completed to show the tack tensile stress to separate the bond formed between titanium substrate surfaces that were adhered using many of the exemplary adhesive compositions listed in in Table 2 during their respective working times. The titanium substrate was prepared as a rectangular block with dimensions of 8.5 mm width×8.5 mm height×20 mm length and the surfaces were polished. For each test, two blocks of titanium were each secured to fixtures that were mounted to an Instron® 5969 axial load frame. One titanium block was mounted to the lower base fixture and the other titanium block was mounted to the upper crosshead fixture. The titanium blocks were mounted in a configuration such that the end face (8.5 mm×8.5 mm) of each titanium block was both parallel and in alignment to the other, but separated by a 10 mm gap. Prior to testing, the titanium end faces that apposed each other were dampened with phosphate buffered saline (PBS) solution. Each exemplary adhesive composition was prepared by mixing for 20 seconds after addition of the water to ensure a smooth consistency in a 25 mL capacity silicone mixing bowl using a stainless steel spatula. After mixing, the composition was spread onto the end face of the lower titanium block. Immediately thereafter, the test was initiated such that the upper crosshead moved down until 5 N of compression force was made between the titanium blocks and held for 10 seconds. During this hold period, excess adhesive composition that had squeezed out of the joint between the blocks during apposition was removed with a spatula. After the hold period, the upper crosshead moved away at 10 mm/min to a gap of 2 mm thus separating from the lower block and the tensile force to separate the titanium blocks was measured. This is referred to as the tack tensile strength. After 10 seconds of delay, the upper crosshead returned to make contact between the upper titanium block and the lower titanium block with 5 N of compression force for 10 seconds, before being separated again at 10 mm/min to a gap of 2 mm thus measuring the tensile force to separate the bond that had formed. This apposition-separation cycle repeated several times over the adhesive composition working time. Table 7 shows the results for the tack tensile stress (kPa) required to separate the bond formed between the titanium blocks through the loading cycle spanning the material working time.

The invention claimed is:

1. An adhesive composition comprising:
   (i) a multivalent metal salt selected from tetracalcium phosphate and tricalcium phosphate;
   (ii) an aqueous medium; and
   (iii) ethylenediamine tetraacetic acid,
   wherein the adhesive strength of the adhesive composition upon curing is greater than 1,000 kPa.

2. The composition of claim 1, wherein the multivalent metal salt is tetracalcium phosphate.

3. The composition of claim 1, wherein the aqueous medium is water.

4. The composition of claim 1, wherein the ethylenediamine tetraacetic acid is present in an amount from about 10% to about 90% weight by weight (w/w) of the total adhesive composition.

5. The composition of claim 1, wherein the composition has a mean particle size of less than 1.000 mm.

6. The composition of claim 1, wherein the composition has a tacky state for up to 12 minutes after mixing with the aqueous medium.

7. The composition of claim 6, wherein the composition during the tacky state has a tack stress of between about 10 kPa and about 250 kPa after mixing with the aqueous medium.

8. The composition of claim 1, wherein the composition has a putty state for up to 15 minutes after mixing with the aqueous medium.

9. The composition of claim 8, wherein the composition during the putty state has a tack stress of between about 10 kPa and about 250 kPa after mixing with the aqueous medium.

10. The composition of claim 1, further comprising an additive.

11. The composition of claim 10, wherein the additive comprises a salt or a viscosity modifier.

12. The composition of claim 10, wherein the additive comprises one or more of a filler, a formulation base, an abrasive, a coloring agent, a flavoring agent, or a polymer.

13. A kit comprising the adhesive composition of claim 1.

14. The kit of claim 13, comprising a device for application of the adhesive composition.

15. The kit of claim 13, comprising a device for preparation of the adhesive composition.

16. An adhesive composition comprising:
   (i) a multivalent metal salt selected from tetracalcium phosphate and tricalcium phosphate;
   (ii) an aqueous medium; and

TABLE 7

Tack Tensile Strength to Separate Bond Formed Between Titanium Blocks Through Loading Cycle Spanning Material Working Time

| Composition | Compound name | Tack Tensile Stress (kPa) to Separate Bond Formed Between Titanium Blocks Through Loading Cycle Spanning Material Working Time | | | | | | | | | |
|---|---|---|---|---|---|---|---|---|---|---|---|
| | | 0-30 sec | 30-60 sec | 60-90 sec | 90-120 sec | 120-150 sec | 150-180 sec | 180-210 sec | 210-240 sec | 240-270 sec | 270-300 sec |
| 1E | EDTA | 10.2 | 16.2 | 19.4 | 13.8 | 25.2 | 13.5 | 32.8 | 41.6 | 24.2 | 16.7 |
| 1G | Malonic Acid | 56.3 | 61.5 | 40.9 | 19.2 | 14.2 | 13.9 | nt | nt | nt | nt |
| 1H | Citric Acid | 84.1 | 85.7 | 96.1 | 103.4 | 108.5 | 103.9 | 130.9 | 123.9 | 131.1 | 137.2 |
| 1I | OPLS | 80.3 | 119.2 | 135.6 | 177.9 | 298.5 | 234.2 | 205.1 | 180.4 | 138.6 | 120.1 | nt = not tested (iii) a compound selected from the group consisting of:
Formula (II-a)
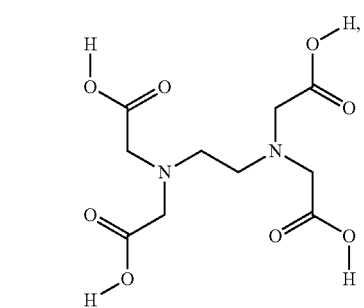
Formula (II-b)
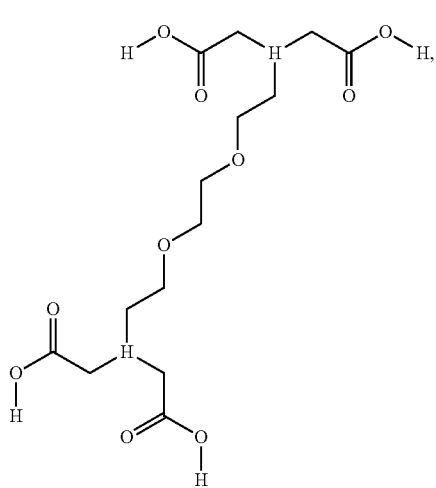
Formula (II-c)
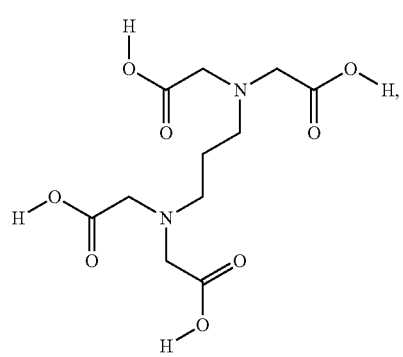
Formula (II-d)
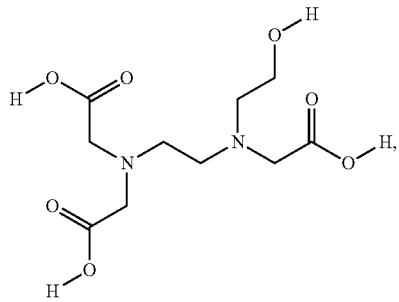
Formula (II-e)
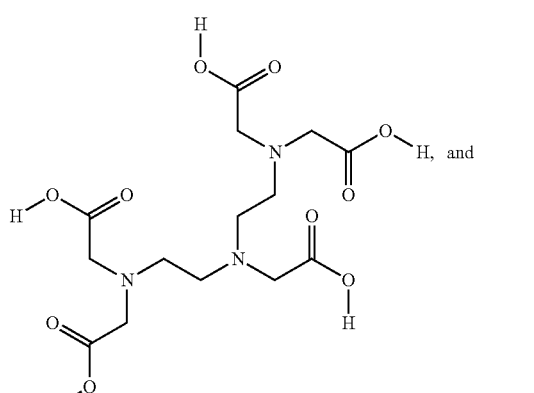
and
Formula (II-f)
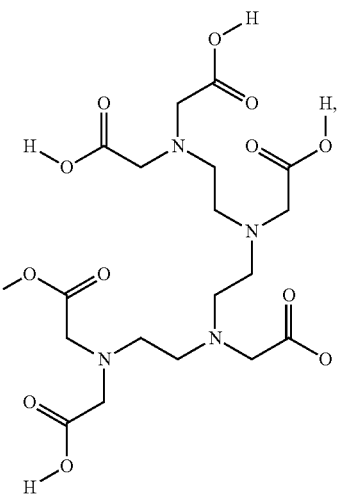
or pharmaceutically acceptable salts thereof,
wherein the adhesive strength of the adhesive composition upon curing is greater than 1,000 kPa.
* * * * *